US012674791B2

(12) United States Patent
Heidebrecht et al.

(10) Patent No.: US 12,674,791 B2
(45) Date of Patent: Jul. 7, 2026

(54) METHODS OF EVALUATING SMALL MOLECULE-MODIFIED POLYMERS IN COMPOSITIONS

(71) Applicant: SIGILON THERAPEUTICS, INC., Cambridge, MA (US)

(72) Inventors: Richard Heidebrecht, Somerville, MA (US); Zoe Yin, Boston, MA (US)

(73) Assignee: SIGILON THERAPEUTICS, INC., Cambridge, MA (US)

( * ) Notice: Subject to any disclaimer, the term of this patent is extended or adjusted under 35 U.S.C. 154(b) by 1137 days.

(21) Appl. No.: 17/764,101

(22) PCT Filed: Sep. 25, 2020

(86) PCT No.: PCT/US2020/052880

§ 371 (c)(1),
(2) Date: Mar. 25, 2022

(87) PCT Pub. No.: WO2021/062273

PCT Pub. Date: Apr. 1, 2021

(65) Prior Publication Data

US 2023/0003706 A1 Jan. 5, 2023

Related U.S. Application Data

(60) Provisional application No. 62/907,400, filed on Sep. 27, 2019.

(51) Int. Cl.
*G01N 33/15* (2006.01)
*A61K 47/61* (2017.01)

(52) U.S. Cl.
CPC ............ *G01N 33/15* (2013.01); *A61K 47/61* (2017.08)

(58) Field of Classification Search
CPC ...... G01N 33/15; A61K 9/5036; A61K 47/61; C08B 37/0084; C08L 5/04
See application file for complete search history.

(56) References Cited

U.S. PATENT DOCUMENTS

| | | | |
|---|---|---|---|
| 3,702,843 | A | 11/1972 | Schweiger |
| 2004/0028745 | A1 | 2/2004 | Bouhadir et al. |
| 2019/0167573 | A1 | 6/2019 | Jarrett et al. |

FOREIGN PATENT DOCUMENTS

| | | | |
|---|---|---|---|
| JP | 2010-209130 | A | 9/2010 |
| WO | 2018/067615 | A1 | 4/2018 |
| WO | 2019/067766 | A1 | 4/2019 |

OTHER PUBLICATIONS

Vegas, Arturo J., et al. "Combinatorial hydrogel library enables identification of materials that mitigate the foreign body response in primates." Nature biotechnology 34.3 (2016): 345-352. (Year: 2016).*

(Continued)

*Primary Examiner* — Robert J Eom
(74) *Attorney, Agent, or Firm* — Quarles & Brady, LLP

(57) ABSTRACT

Described herein are methods for evaluating polymer compositions comprising polymers modified with a small molecule compound (e.g., afibrotic compound), including methods for determining the concentration levels of said compounds.

20 Claims, 2 Drawing Sheets

(56) References Cited

OTHER PUBLICATIONS

Zhang, Hu, et al. "HPLC-MS/MS enantioseparation of triazole fungicides using polysaccharide-based stationary phases." Journal of Separation Science 35.7 (2012): 773-777. (Year: 2012).*

Cheong et al., "A rapid and accurate method for the quantitative estimation of natural polysaccharides and their fractions using high performance size exclusion chromatography coupled with multi-angle laser light scattering and refractive index detector" Journal of Chromatography A, vol. 1400, 2015, pp. 98-106.

Jin et al., "Microwave-triggered smart drug release from liposomes co-encapsulating doxorubicin and salt for local combined hyper-thermia and chemotherapy of cancer" Bioconjugate Chemistry, vol. 27, 2016, pp. 2931-2942.

Padilla et al., "Polyester dendritic systems for drug delivery applications: In vitro and in vivo evaluation" Bioconjugate Chemistry, vol. 13, 2002, pp. 453-461.

International Search Report and Written Opinion for Application No. PCT/US2020/052880 mailed Feb. 23, 2021.

Freire et al., "An efficient method for determination of the degree of substitution of cellulose esters of long chain aliphatic acids" Cellulose, 2005, vol. 12, No. 5, pp. 449-458.

Souza et al., "Development of a HPLC method for determination of four UV filters in sunscreen and its application to skin penetration studies" Biomedical Chromatography, 2017, vol. 31, No. 12, pp. 1-8.

* cited by examiner

METHODS OF EVALUATING SMALL MOLECULE-MODIFIED POLYMERS IN COMPOSITIONS

CLAIM OF PRIORITY

This application is a U.S. national phase application and claims the benefit of priority under 35 U.S.C. § 371 of International Application No. PCT/US2020/052880, filed on Sep. 25, 2020, which claims priority to U.S. Provisional Application No. 62/907,400, filed Sep. 27, 2019. The disclosure of each of the foregoing applications is incorporated herein by reference in its entirety.

BACKGROUND

Treating chronic and genetic diseases by implanting cells engineered to produce a therapeutic substance capable of treating such diseases has exciting potential to improve the health of patients with such diseases. To fully achieve this potential, the implanted cells must be protected from the patient's immune response, so that they remain viable, and the implanted cells must also be capable of producing therapeutic levels of the desired therapeutic substance for several weeks, months or even longer. One approach for delivering such cellular therapies is to encapsulate the engineered cells into semi-permeable devices (e.g., hydrogel capsules), with the objective that the device structure isolates the cells from host immune system cells, while allowing entry of nutrients for the cells and exit of the produced therapeutic substances. In some cases, these semi-permeable devices (e.g., hydrogel capsules) may be modified with various substances, including small molecule compounds. A need exists to improve methods of evaluating these semi-permeable devices (e.g., hydrogel capsules), for example, by quantifying the concentration of the small molecule compounds bound to the devices, which can affect the long term stability of the devices and their ability to evade the host foreign body response (FBR) when implanted into a subject.

SUMMARY

The present disclosure provides, at least in part, methods for evaluating a polymer composition comprising a polymer modified with a small molecule compound. In an embodiment, the evaluating comprises determining the concentration of the small molecule compound within the polymer composition. The polymer compositions may be used to prepare semi-permeable devices (e.g., hydrogel capsules) that comprise at least one compartment encapsulating a plurality of cells capable of expressing a therapeutic agent, which may be released from the device, e.g., upon implantation in a subject. In an embodiment, certain small molecule compounds bound to the modified polymer are capable of mitigating the host foreign body response (FBR) of the polymer composition and/or semi-permeable device. For example, polymer compositions and semi-permeable devices comprising certain small molecule compounds have exhibited a lower host FBR compared with the host FBR induced by polymer compositions and semi-permeable device that do not contain said small molecule compounds.

Without wishing to be bound by theory, the concentration of certain small molecule compounds (e.g., afibrotic compounds) within polymer compositions used to prepare a semi-permeable device can have a significant impact on the ability of the composition and/or device to mitigate the host FBR. As such, it may be useful to determine the concentration of the small molecule compound contained within the polymer compositions in order to, for example, modulate the FBR as needed. However, current methods for quantifying the concentration of certain small molecules are not ideal for use in evaluating the polymer compositions described herein. The methods described below are designed to circumvent these obstacles and provide the concentration of certain small molecule compounds of a modified polymer within a polymer composition in a reliable manner.

In one aspect, the present disclosure features a method of evaluating a polymer composition comprising a polymer modified with a small molecule compound, the method comprising subjecting the polymer composition to reaction conditions that allow for release of the small molecule compound from the modified polymer. The method may further comprise acquiring a value of the concentration of the small molecule compound bound to the modified polymer. In an embodiment, the polymer in the modified polymer is a polysaccharide. In an embodiment, the polysaccharide is an alginate (e.g., having an average molecular weight of 75 kD to 150 kD and/or a guluronate to mannuronate (G:M) ratio of greater than or equal to 1.5).

The small molecule compound may be covalently bound or non-covalently bound to the polymer (e.g., alginate) in the modified polymer. In some embodiments, the small molecule compound is covalently bound to the polymer (e.g., alginate), e.g., through an attachment group. In an embodiment, the small molecule is an afibrotic compound. In an embodiment, the afibrotic compound is a compound of Formula (I):

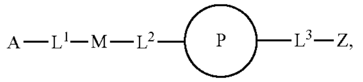

(I)

or a pharmaceutically acceptable salt thereof, wherein the variables A, $L^1$, M, $L^2$, P, $L^3$, and Z, as well as related subvariables, are defined herein. In some embodiments, the compound of Formula (I) or a pharmaceutically acceptable salt thereof (e g, Formulas (I-a), (II), (II-a), (II-b), (III), (III-a), (III-b), (III-c), (III-d), or (III-e)) is a compound described herein, including for example, one of the compounds shown in Table 1 herein. In an embodiment, the afibrotic compound is Compound 100, Compound 101 or Compound 102 shown in Table 1.

In some embodiments, the reaction conditions that allow for release of the small molecule compound from the modified polymer comprise contacting the polymer with an acidic solution, a basic solution, an enzymatic solution, light, microwave irradiation, heat, or a combination thereof. In an embodiment, the method further comprises a separation step, which can occur prior to acquiring the concentration of the small molecule compound. Exemplary separation steps include filtration or chromatography (e.g., size-exclusion chromatography, ion-exchange chromatography, reversed-phase chromatography, gel filtration chromatography, or hydrophobic interaction chromatography). In an embodiment, acquiring a value for the concentration of a small molecule compound comprises determining the area of a chromatogram peak for the small molecule compound. In an embodiment, acquiring the concentration of a value for the concentration of a small molecule compound entails comparison to a standard (e.g., a small molecule compound, e.g. a compound of Formula (I)). The concentration of a small molecule compound bound to a modified polymer may range, for example from 0.5% and 10% (w/w) modified polymer, e.g., between about 0.5% and 5%, 1% and 5%, 1% and 4%, or 1 and 3% (w/w) modified polymer.

In an embodiment, the method further comprises acquiring the concentration of unconjugated small molecule compound (i.e., "free" small molecule compound) in the polymer composition. The concentration of free small molecule compound (e.g., free afibrotic compound) in the polymer composition may be less than about 1% (w/w) modified polymer, e.g., less than about 0.9%, 0.8%, 0.7%, 0.6%, or 0.5% (w/w) modified polymer.

In another aspect, the present disclosure features a method of evaluating a polymer composition comprising a polymer modified with a small molecule compound (e.g., a modified polymer), wherein the method does not comprise subjecting the polymer compositions to reaction conditions that allow for release of the small molecule compound from the modified polymer. In an embodiment, the method further comprises acquiring a value of the total small molecule compound conjugated (e.g., covalently bound) to the modified polymer in the polymer composition; and using the values obtained to acquire a value for the concentration of the modified polymer, thereby evaluating the polymer composition. In an embodiment, the modified polymer is a modified polysaccharide. In an embodiment, the polymer in the modified polymer (e.g., the polymer used to prepare the modified polymer) is an alginate (e.g., having an average molecular weight of 75 kD to 150 kD and/or a guluronate to mannuronate (G:M) ratio of greater than or equal to 1.5). In an embodiment, the small molecule compound is an afibrotic compound. In an embodiment, the afibrotic compound is a compound of Formula (I) or a pharmaceutically acceptable salt thereof, e.g., as described herein. In an embodiment, the method comprises acquiring a value for the refractive index of the polymer composition. In an embodiment, acquiring the value of the refractive index comprises acquiring a refractometer reading (nD) at a specific wavelength and/or specific temperature.

In another aspect, the present disclosure features modified polymers and polymer compositions comprising a concentration of one or more small molecule compounds of between about 0.5% and 5%, 1% and 5%, 1% and 4%, or 1 and 3% (w/w) modified polymer.

The details of one or more embodiments of the disclosure are set forth herein. Other features, objects, and advantages of the disclosure will be apparent from the Detailed Description, the Figures, the Examples, and the Claims.

BRIEF DESCRIPTION OF DRAWINGS

FIG. 2A shows the UV chromatogram corresponding to the standard solution, while FIG. 2B shows a UV chromatogram corresponding to the free afibrotic compound in solution.

DETAILED DESCRIPTION

Figure 1:
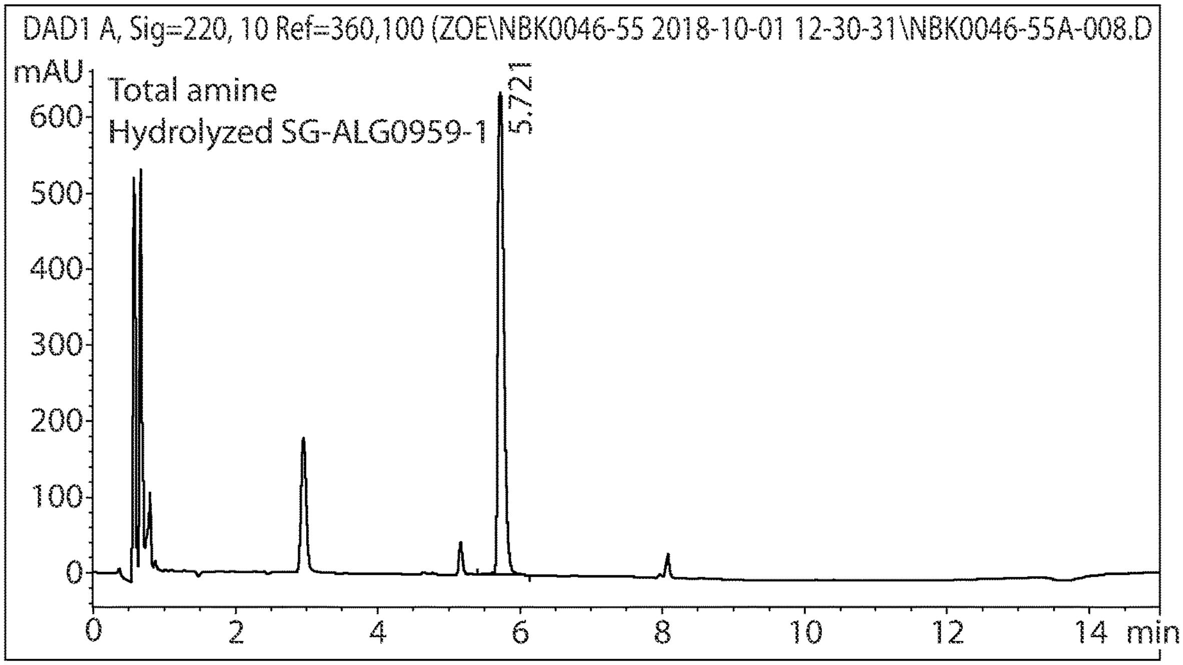
FIG. 1 depicts an exemplary HPLC chromatogram (UV) acquired in the determination of the level of total afibrotic compound in a sample of afibrotic alginate, as outlined in Example 2.

The present disclosure features methods for evaluating polymer compositions which comprise at least one polymer modified by a small molecule compound, such as an afibrotic compound. The polymer compositions may be used to encapsulate a plurality of cells (e.g., live cells) capable of expressing a therapeutic agent when the device is implanted into a subject (e.g., a human). In an embodiment, the polymer compositions and devices are capable of mitigating the host FBR. In an embodiment, the polymer compositions and devices further comprise a means for improving the viability and/or productivity of living cells contained therein.

In an embodiment, the polymer compositions are evaluated by quantifying the concentration of a small molecule compound that is bound (covalently or non-covalently) to a polymer in the polymer composition. The concentration of the bound small molecule compound may be evaluated, for example, by acquiring a value of the total concentration of the small molecule compound (bound and unbound) in a first sample of the polymer composition (i.e., the "total small molecule"), acquiring a value of the concentration of unbound small molecule compound (i.e., the "free small molecule) in a second sample of the polymer composition, and subtracting the concentration of the free small molecule from the concentration of the total small molecule. In another embodiment, the polymer composition is evaluated by acquiring a value of the refractive index of the polymer composition. The polymer composition may or may not be subjected to conditions to hydrolyze the small molecule compound from the modified polymer. Methods for determining the small molecule compound concentration within polymer compositions are described herein.

Abbreviations and Definitions

Throughout the detailed description and examples of the disclosure the following abbreviations will be used:

CBP cell-binding polypeptide
CBP-polymer polymer covalently modified with a CBP via a linker
CM-Alg chemically modified alginate
CM-LMW-Alg chemically modified, low molecular weight alginate
CM-HMW-Alg chemically modified, high molecular weight alginate
CM-MMW-Alg chemically modified, medium molecular weight alginate
HMW-Alg high molecular weight alginate
MMW-Alg medium molecular weight alginate
RGD-alginate an alginate covalently modified with a peptide comprising the amino acid sequence RGD
U-Alg unmodified alginate
U-HMW-Alg unmodified high molecular weight alginate
U-LMW-Alg unmodified low molecular weight alginate
U-MMW-Alg unmodified medium molecular weight alginate
70:30 CM-Alg:U-Alg 70:30 mixture (V:V) of a chemically modified alginate and an unmodified alginate, e.g., as described in Example 2

So that the disclosure may be more readily understood, certain technical and scientific terms used herein are specifically defined below. Unless specifically defined elsewhere in this document, all other technical and scientific terms used herein have the meaning commonly understood by one of ordinary skill in the art to which this disclosure belongs.

As used herein, including the appended claims, the singular forms of words such as "a," "an," and "the," include their corresponding plural references unless the context clearly dictates otherwise.

"About" or "approximately" means when used herein to modify a numerically defined parameter (e.g., a physical description of a hydrogel capsule such as diameter, sphericity, number of cells encapsulated therein, the number of capsules in a preparation), means that the recited numerical value is within an acceptable functional range for the defined parameter as determined by one of ordinary skill in the art, which will depend in part on how the numerical value is measured or determined, e.g., the limitations of the measurement system, including the acceptable error range for that measurement system. For example, "about" can mean a range of 20% above and below the recited numerical value. In some embodiments, the term "about" means that the modified parameter may vary by as much as 15%, 10% or 5% above and below the stated numerical value for that parameter. Alternatively, particularly with respect to certain properties of the devices described herein, such as density of a small molecule compound of a polymer composition, the term "about" can mean within an order of magnitude above and below the recited value, e.g., within 5-fold, 4-fold, 3-fold, 2-fold or 1-fold.

"Acquire" or "acquiring", as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third-party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., using a fluorescence microscope to acquire fluorescence microscopy data or using a refractometer to acquire a refractive index value.

"Administer", "administering", or "administration", as used herein, refer to implanting, absorbing, ingesting, injecting or otherwise introducing into a subject, an entity described herein (e.g., a device or a preparation of devices), or providing such an entity to a subject for administration.

"Afibrotic", as used herein, means a compound or material that mitigates the foreign body response (FBR). For example, the amount of FBR in a biological tissue that is induced by implant into that tissue of a device (e.g., hydrogel capsule) comprising an afibrotic compound is lower than the FBR induced by implantation of an afibrotic-null reference device, i.e., a device that lacks any afibrotic compound, but is of substantially the same composition (e.g., same CBP-polymer, same cell type(s)) and structure (e.g., size, shape, no. of compartments). In an embodiment, the degree of the FBR is assessed by the immunological response in the tissue containing the implanted device (e.g., hydrogel capsule), which may include, for example, protein adsorption, macrophages, multinucleated foreign body giant cells, fibroblasts, and angiogenesis, using assays known in the art, e.g., as described in WO 2017/075630, or using one or more of the assays/methods described Vegas, A., et al., Nature Biotechnol (supra), (e.g., subcutaneous cathepsin measurement of implanted capsules, Masson's trichrome (MT), hematoxylin or eosin staining of tissue sections, quantification of collagen density, cellular staining and confocal microscopy for macrophages (CD68 or F4/80), myofibroblasts (alpha-muscle actin, SMA) or general cellular deposition, quantification of 79 RNA sequences of known inflammation factors and immune cell markers, or FACS analysis for macrophage and neutrophil cells on retrieved devices (e.g., capsules) after 14 days in the intraperitoneal space of a suitable test subject, e.g., an immunocompetent mouse. In an embodiment, the FBR is assessed by measuring the levels in the tissue containing the semi-permeable device of one or more biomarkers of immune response, e.g., cathepsin, IL-13, IL-6, G-CSF, GM-CSF, IL-4, CCL2, or CCL4. In some embodiments, the FBR induced by a semi-permeable device of the invention (e.g., a hydrogel capsule comprising an afibrotic compound disposed on its outer surface), is at least about 80%, about 85%, about 90%, about 95%, about 99%, or about 100% lower than the FBR induced by an FBR-null reference device, e.g., a semi-permeable device that is substantially identical to the test or claimed device except for lacking the means for mitigating the FBR (e.g., a hydrogel capsule that does not comprise an afibrotic compound but is otherwise substantially identical to the claimed capsule. In some embodiments, the FBR (e.g., level of a biomarker(s)) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer.

"Cell," as used herein, refers to an engineered cell or a cell that is not engineered. In an embodiment, a cell is an immortalized cell or an engineered cell derived from an immortalized cell. In an embodiment, the cell is a live cell, e.g., is viable as measured by any technique described herein or known in the art.

"Cell-binding peptide (CBP)", as used herein, means a linear or cyclic peptide that comprises an amino acid sequence that is derived from the cell binding domain of a ligand for a cell-adhesion molecule (CAM) (e.g., that mediates cell-matrix junctions or cell-cell junctions). In an embodiment, the CBP is capable of mimicking at least one activity of a ligand for a cell-adhesion molecule (CAM) or other cell-surface molecule that mediates cell-matrix junctions or cell-cell junctions or other receptor-mediated signaling. The CBP may be less than 50, 40 30, 25, 20, 15 or 10 amino acids in length. In an embodiment, the CBP is between 3 and 12 amino acids in length, 4 and 10 amino acids in length, or is 3, 4, 5, 6, 7 8, 9 or 10 amino acids in length. The CBP amino acid sequence may be identical to the naturally occurring binding domain sequence or may be a conservatively substituted variant thereof. In an embodiment, the CAM ligand is a mammalian protein. In an embodiment, the CBP is an RGD peptide, which means the peptide comprises the amino acid sequence RGD and optionally comprises one or more additional amino acids located at one or both of the N-terminus and C-terminus. In an embodiment, the CBP is a cyclic peptide comprising RGD, e.g., one of the cyclic RGD peptides described in Vilaca, H. et al., *Tetrahedron* 70 (35):5420-5427 (2014). In an embodiment, the CBP is a linear peptide comprising RGD and is less than 6 amino acids in length. In an embodiment, the CBP is a linear peptide that consists essentially of RGD or RGDSP.

"CBP-polymer", as used herein, means a polymer comprising at least one CBP covalently attached to the polymer via a linker. In an embodiment, the polymer is not a peptide or a polypeptide. In an embodiment, the polymer in a CBP-polymer does not contain any amino acids. In an embodiment, the polymer in a CBP-polymer is a synthetic or naturally occurring polysaccharide, e.g., an alginate, e.g., a sodium alginate. In an embodiment, the number of polysaccharide moieties with a covalently attached CBP is less than any of the following values: 99%, 95%, 90%, 80%, 70%, 60%, 50%, 40% 30%, 20%, 10%, 5%, 1%.

"Consists essentially of", and variations such as "consist essentially of" or "consisting essentially of" as used throughout the specification and claims, indicate the inclusion of any recited elements or group of elements, and the optional inclusion of other elements, of similar or different nature than the recited elements, that do not materially change the basic or novel properties of the specified molecule, composition, device, or method. As a non-limiting example, a peptide or polypeptide that consists essentially of a recited amino acid sequence may also include one or more amino acids, including substitutions in the recited amino acid sequence, of one or more amino acid residues, which do not materially affect the relevant biological activity of the cell-binding peptide or the therapeutic protein, respectively. As another non-limiting example, a peptide or polypeptide that consists essentially of a recited amino acid sequence may contain one or more covalently attached moieties (e.g., a radioactive or fluorescent label) that do not materially change the relevant biological activity of the cell-binding peptide, e.g., its ability to increase the viability or productivity of encapsulated cells as described herein.

"Derived from", as used herein with respect to cells, refers to cells obtained from tissue, cell lines, or cells, which optionally are then cultured, passaged, differentiated, induced, etc. to produce the derived cells. For example, mesenchymal stem cells can be derived from mesenchymal tissue and then differentiated into a variety of cell types.

"Device", as used herein, refers to any implantable object (e.g., a particle, a hydrogel capsule, an implant, a medical device), which contains cells (e.g., live cells) capable of expressing a therapeutic agent following implant of the device, and has a configuration that supports the viability of the cells by allowing cell nutrients to enter the device. In some embodiments, the device is a semi-permeable device, wherein it allows release from the device of metabolic byproducts and/or the therapeutic agent generated by the live cells.

"Effective amount", as used herein, refers to an amount of a device, a device composition, or a component of the device or device composition, e.g, a plurality of hydrogel capsules comprising a cell, e.g., an engineered cell, or an agent, e.g., a therapeutic agent, produced by a cell sufficient to elicit a biological response, e.g., to treat a disease, disorder, or condition. In some embodiments, the term "effective amount" refers to the amount of a component of the device, e.g., number of cells in the device, the concentration of an afibrotic compound disposed on the surface and/or in a barrier compartment of the device, or the concentration of a polypeptide (e.g., a CBP) in the cell-containing compartment. As will be appreciated by those of ordinary skill in this art, the effective amount may vary depending on such factors as the desired biological endpoint, the pharmacokinetics of the therapeutic agent, composition or device (e.g., capsule, particle), the condition being treated, the mode of administration, and the age and health of the subject. An effective amount encompasses therapeutic and prophylactic treatment. As an example, an effective amount of a small molecule compound (e.g., an afibrotic compound) bound to a modified polymer in a semi-permeable device may modulate the host FBR. An effective amount of a device, composition or component, e.g., a small molecule compound, may be determined by any technique known in the art or described herein.

"Engineered cell," as used herein, is a cell having a non-naturally occurring alteration, and typically comprises a nucleic acid sequence (e.g., DNA or RNA) or a polypeptide not present (or present at a different level than) in an otherwise similar cell under similar conditions that is not engineered (an exogenous nucleic acid sequence). In an embodiment, an engineered cell comprises an exogenous nucleic acid (e.g., a vector or an altered chromosomal sequence). In an embodiment, an engineered cell comprises an exogenous polypeptide or an exogenous nucleic acid sequence, e.g., a sequence, e.g., DNA or RNA, not present in a similar cell that is not engineered. In an embodiment, the exogenous nucleic acid sequence is chromosomal, e.g., the exogenous nucleic acid sequence is an exogenous sequence disposed in endogenous chromosomal sequence. In an embodiment, the exogenous nucleic acid sequence is chromosomal or extra chromosomal, e.g., a non-integrated vector. In an embodiment, the exogenous nucleic acid sequence comprises a chromosomal or extra-chromosomal nucleic acid sequence, which comprises a sequence that encodes a polypeptide, or which is expressed as a polypeptide. In an embodiment, an engineered cell comprises a therapeutic agent present at a level or distribution which differs from the level found in a similar cell that has not been engineered. In an embodiment, an engineered cell comprises an RPE engineered to produce an RNA or a therapeutic polypeptide. For example, an engineered cell may comprise an exogenous nucleic acid sequence comprising a chromosomal or extra-chromosomal exogenous nucleic acid sequence that comprises a sequence which is expressed as RNA, e.g., mRNA or a regulatory RNA. In an embodiment, an engineered cell comprises an exogenous nucleic acid sequence that comprises a chromosomal or extra-chromosomal nucleic acid sequence comprising a sequence that encodes a polypeptide, or which is expressed as a polypeptide. In an embodiment, the polypeptide is encoded by a codon optimized sequence to achieve higher expression of the polypeptide than a naturally occurring coding sequence. The codon optimized sequence may be generated using a commercially available algorithm, e.g., GeneOptimizer (ThermoFisher Scientific), OptimumGene™ (GenScript, Piscataway, NJ USA), GeneGPS® (ATUM, Newark, CA USA), or Java Codon Adaptation Tool (JCat, www.jcat.de, Grote, A. et al., Nucleic Acids Research, Vol 33, Issue suppl_2, pp. W526-W531 (2005). In an embodiment, an engineered cell (e.g., an RPE cell) comprises an exogenous nucleic acid sequence that modulates the conformation or expression of an endogenous sequence. In an embodiment, an engineered cell (e.g., RPE cell) is cultured from a population of stably transfected cells, or from a monoclonal cell line.

"Factor VII protein" or "FVII protein" as used herein, means a polypeptide that comprises the amino acid sequence of a naturally occurring factor VII protein or variant thereof that has a FVII biological activity, e.g., promoting blood clotting, as determined by an art-recognized assay, unless otherwise specified. Naturally occurring FVII exists as a single chain zymogen, a zymogen-like two-chain polypeptide and a fully activated two-chain form (FVIIa). In some embodiments, reference to FVII includes single-chain and two-chain forms thereof, including zymogen-like and FVIIa. FVII proteins that may be produced by a device described herein, e.g., a device containing engineered RPE cells, include wild-type primate (e.g., human), porcine, canine, and murine proteins, as well as variants of such wild-type proteins, including fragments, mutants, variants with one or more amino acid substitutions and/or deletions. In some embodiments, a variant FVII protein is capable of being activated to the fully activated two-chain form (Factor VIIa) that has at least 50%, 75%, 90% or more (including >100%) of the activity of wild-type Factor Vila. Variants of FVII and FVIIa are known, e.g., marzeptacog alfa (activated) (MarzAA) and the variants described in European Patent No. 1373493, U.S. Pat. Nos. 7,771,996, 9,476,037 and US published application No. US20080058255.

Factor VII biological activity may be quantified by an art recognized assay, unless otherwise specified. For example, FVII biological activity in a sample of a biological fluid, e.g., plasma, may be quantified by (i) measuring the amount of Factor Xa produced in a system comprising tissue factor (TF) embedded in a lipid membrane and Factor X (Persson et al., *J. Biol. Chem.* 272:19919-19924, 1997); (ii) measuring Factor X hydrolysis in an aqueous system; (iii) measuring its physical binding to TF using an instrument based on surface plasmon resonance (Persson, *FEBS Letts.* 413:359-363, 1997); or (iv) measuring hydrolysis of a synthetic substrate; and/or (v) measuring generation of thrombin in a TF-independent in vitro system. In an embodiment, FVII activity is assessed by a commercially available chromogenic assay (BIOPHEN FVII, HYPHEN BioMed Neuville sur Oise, France), in which the biological sample containing FVII is mixed with thromboplastin calcium, Factor X and SXa-11 (a chromogenic substrate specific for Factor Xa).

"Factor VIII protein" or "FVIII protein" as used herein, means a polypeptide that comprises the amino acid sequence of a naturally occurring factor VIII polypeptide or variant thereof that has an FVIII biological activity, e.g., coagulation activity, as determined by an art-recognized assay, unless otherwise specified. FVIII proteins that may be expressed by a device described herein, e.g., a device containing engineered RPE cells, include wild-type primate (e.g., human), porcine, canine, and murine proteins, as well as variants of such wild-type proteins, including fragments, mutants, variants with one or more amino acid substitutions and/or deletions, B-domain deletion (BDD) variants, single chain variants and fusions of any of the foregoing wild-type or variants with a half-life extending polypeptide. In an embodiment, the cells are engineered to encode a precursor factor VIII polypeptide (e.g., with the signal sequence) with a full or partial deletion of the B domain. In an embodiment, the cells are engineered to encode a single chain factor VIII polypeptide which contains a variant FVIII protein preferably has at least 50%, 75%, 90% or more (including >100%) of the coagulation activity of the corresponding wild-type factor VIII. Assays for measuring the coagulation activity of FVIII proteins include the one stage or two stage coagulation assay (Rizza et al., 1982, Coagulation assay of FVIII:C and FIXa in Bloom ed. The Hemophelias. NY Churchill Livingston 1992) or the chromogenic substrate FVIII:C assay (Rosen, S. 1984. *Scand J Haematol* 33:139-145, suppl.).

Figure 2A:
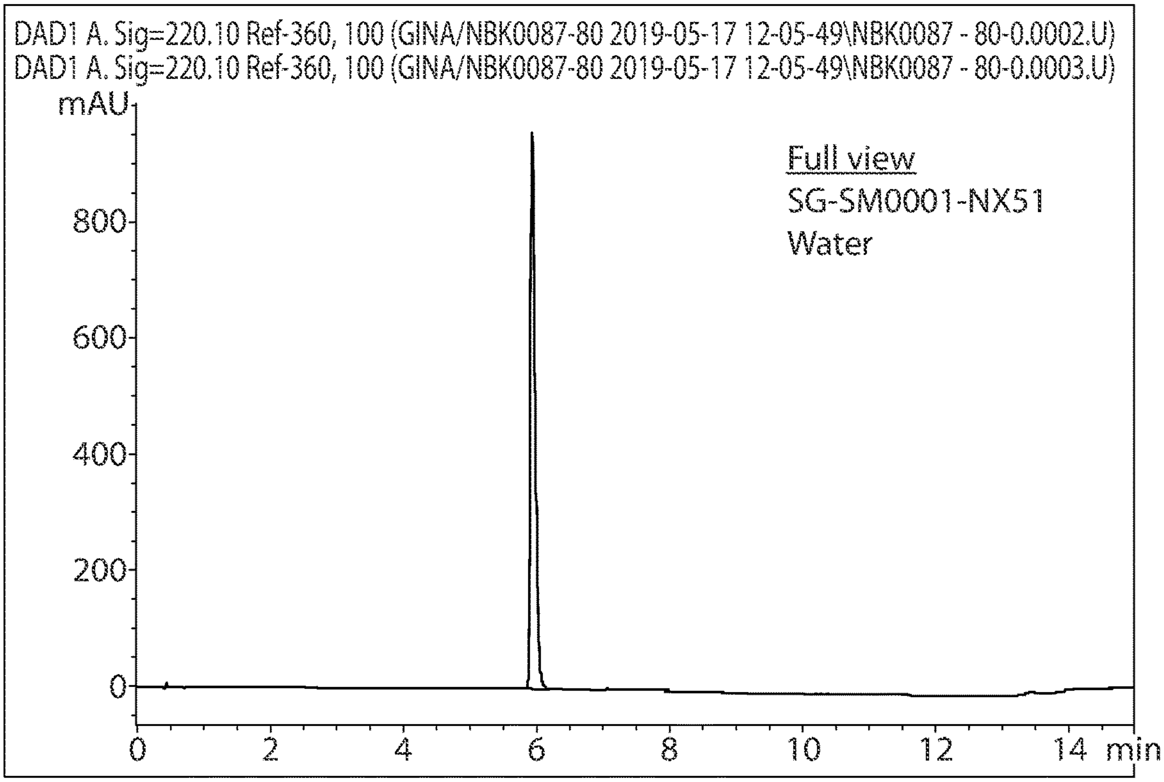
FIGS. 2A-2B depict exemplary HPLC chromatograms acquired in the determination of the level of unconjugated (e.g., free) afibrotic compound in a sample of an afibrotic alginate, as outlined in Example 3.

A number of FVIII-BDD variants are known, and include, e.g., variants with the full or partial B-domain deletions disclosed in any of the following U.S. Pat. No. 4,868,112 (e.g., col. 2, line 2 to col. 19, line 21 and table 2); U.S. Pat. No. 5,112,950 (e.g., col. 2, lines 55-68, FIG. 2, and example 1); U.S. Pat. No. 5,171,844 (e.g., col. 4, line 22 to col. 5, line 36); 5,543,502 (e.g., col. 2, lines 17-46); U.S. Pat. Nos. 5,595,886; 5,610,278; 5,789,203 (e.g., col. 2, lines 26-51 and examples 5-8); 5,972,885 (e.g., col. 1, lines 25 to col. 2, line 40); 6,048,720 (e.g., col. 6, lines 1-22 and example 1); U.S. Pat. Nos. 6,060,447; 6,228,620; 6,316,226 (e.g., col. 4, line 4 to col. 5, line 28 and examples 1-5); U.S. Pat. Nos. 6,346,513; 6,458,563 (e.g., col. 4, lines 25-53) and 7,041,635 (e.g., col. 2, line 1 to col. 3, line 19, col. 3, line 40 to col. 4, line 67, col. 7, line 43 to col. 8, line 26, and col. 11, line 5 to col. 13, line 39). In some embodiments, a FVIII-BDD protein produced by a device described herein (e.g., expressed by engineered cells contained in the device) has one or more of the following deletions of amino acids in the B-domain: (i) most of the B domain except for amino-terminal B-domain sequences essential for intracellular processing of the primary translation product into two polypeptide chains (WO 91/09122); (ii) a deletion of amino acids 747-1638 (Hoeben R. C., et al. *J. Biol. Chem.* 265 (13): 7318-7323 (1990)); amino acids 771-1666 or amino acids 868-1562 (Meulien P., et al. *Protein Eng.* 2(4):301-6 (1988); amino acids 982-1562 or 760-1639 (Toole et al., *Proc. Natl. Acad. Sci. U.S.A.* 83:5939-5942 (1986)); amino acids 797-1562 (Eaton et al., *Biochemistry* 25:8343-8347 (1986)); 741-1646 (Kaufman, WO 87/04187)), 747-1560 (Sarver et al., DNA 6:553-564 (1987)); amino acids 741-1648 (Pasek, WO 88/00831)), amino acids 816-1598 or 741-1689 (Lagner (Behring Inst. Mitt. (1988) No 82:16-25, EP 295597); a deletion that includes one or more residues in a furin protease recognition sequence, e.g., LKRHQR (SEQ ID NO: 65) at amino acids 1643-1648, including any of the specific deletions recited in U.S. Pat. No. 9,956,269 at col. 10, line 65 to col. 11, line 36.

In other embodiments, a FVIII-BDD protein retains any of the following B-domain amino acids or amino acid sequences: (i) one or more N-linked glycosylation sites in the B-domain, e.g., residues 757, 784, 828, 900, 963, or optionally 943, first 226 amino acids or first 163 amino acids (Miao, H. Z., et al., Blood 103(a): 3412-3419 (2004), Kasuda, A., et al., *J. Thromb. Haemost.* 6: 1352-1359 (2008), and Pipe, S. W., et al., *J. Thromb. Haemost.* 9: 2235-2242 (2011).

In some embodiments, the FVIII-BDD protein is a single-chain variant generated by substitution of one or more amino acids in the furin protease recognition sequence (LKRHQR (SEQ ID NO: 65) at amino acids 1643-1648) that prevents proteolytic cleavage at this site, including any of the substitutions at the R1645 and/or R1648 positions described in U.S. Pat. Nos. 10,023,628, 9,394,353 and 9,670,267.

In some embodiments, any of the above FVIII-BDD proteins may further comprise one or more of the following variations: a F309S substitution to improve expression of the FVIII-BDD protein (Miao, H. Z., et al., Blood 103(a): 3412-3419 (2004); albumin fusions (WO 2011/020866); and Fc fusions (WO 04/101740).

All FVIII-BDD amino acid positions referenced herein refer to the positions in full-length human FVIII, unless otherwise specified.

"Factor IX protein" or "FIX protein", as used herein, means a polypeptide that comprises the amino acid sequence of a naturally occurring factor IX protein or variant thereof that has a FIX biological activity, e.g., coagulation activity, as determined by an art-recognized assay, unless otherwise specified. FIX is produced as an inactive zymogen, which is converted to an active form by factor XIa excision of the activation peptide to produce a heavy chain and a light chain held together by one or more disulfide bonds. FIX proteins that may be produced by devices described herein (e.g., a semi-permeable device containing engineered RPE cells) include wild-type primate (e.g., human), porcine, canine, and murine proteins, as well as variants of such wild-type proteins, including fragments, mutants, variants with one or more amino acid substitutions and/or deletions and fusions of any of the foregoing wild-type or variant proteins with a half-life extending polypeptide. In an embodiment, cells are engineered to encode a full-length wild-type human factor IX polypeptide (e.g., with the signal sequence) or a functional variant thereof. A variant FIX protein preferably has at least 50%, 75%, 90% or more (including >100%) of the coagulation activity of wild-type factor VIX. Assays for measuring the coagulation activity of FIX proteins include the Biophen Factor IX assay (Hyphen BioMed) and the one stage clotting assay (activated partial thromboplastin time (aPTT), e.g., as described in EP 2 032 607, thrombin generation time assay (TGA) and rotational thromboelastometry, e.g., as described in WO 2012/006624.

A number of functional FIX variants are known and may be expressed by engineered cells encapsulated in a device described herein, including any of the functional FIX variants described in the following international patent publications: WO 02/040544 at page 4, lines 9-30 and page 15, lines 6-31; WO 03/020764 in Tables 2 and 3 at pages 14-24, and at page 12, lines 1-27; WO 2007/149406 at page 4, line 1 to page 19, line 11; WO 2007/149406 A2 at page 19, line 12 to page 20, line 9; WO 08/118507 at page 5, line 14 to page 6, line 5; WO 09/051717 at page 9, line 11 to page 20, line 2; WO 09/137254 at page 2, paragraph [006] to page 5, paragraph [011] and page 16, paragraph [044] to page 24, paragraph [057]; WO 09/130198 A2 at page 4, line 26 to page 12, line 6; WO 09/140015 at page 11, paragraph [0043] to page 13, paragraph [0053]; WO 2012/006624; WO 2015/086406.

In certain embodiments, the FIX polypeptide comprises a wild-type or variant sequence fused to a heterologous polypeptide or non-polypeptide moiety extending the half-life of the FIX protein. Exemplary half-life extending moieties include Fc, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, albumin-binding small molecules, or any combination thereof. An exemplary FIX polypeptide is the rFIXFc protein described in WO 2012/006624, which is an FIXFc single chain (FIXFc-sc) and an Fc single chain (Fc-sc) bound together through two disulfide bonds in the hinge region of Fc.

FIX variants also include gain and loss of function variants. An example of a gain of function variant is the "Padua" variant of human FIX, which has a L (leucine) at position 338 of the mature protein instead of an R (arginine) (corresponding to amino acid position 384 of SEQ ID NO:2), and has greater catalytic and coagulant activity compared to wild-type human FIX (Chang et al., J. Biol. Chem., 273:12089-94 (1998)). An example of a loss of function variant is an alanine substituted for lysine in the fifth amino acid position from the beginning of the mature protein, which results in a protein with reduced binding to collagen IV (e.g., loss of function). "Interleukin-2 protein" or "IL-2 protein", as used herein means a polypeptide comprising the amino acid sequence of a naturally-occurring IL-2 protein or variant thereof that has an IL-2 biological activity, e.g., activate IL-2 receptor signaling in Treg cells, as determined by an art-recognized assay, unless otherwise specified. IL-2 proteins that may be produced by a device described herein, e.g., a device containing engineered RPE cells, include wild-type primate (e.g., human), porcine, canine, and murine proteins, as well as variants of such wild-type proteins. A variant IL-2 protein preferably has at least 50%, 75%, 90% or more (including >100%) of the biological activity of the corresponding wild-type IL-2. Biological activity assays for IL-2 proteins are described in U.S. Pat. No. 10,035,836, and include, e.g., measuring the levels of phosphorylated STATS protein in Treg cells compared to CD4+CD25−/low T cells or NK cells. Variant IL-2 proteins that may be produced by a device of the present disclosure (e.g., a device containing engineered RPE cells) include proteins with one or more of the following amino acid substitutions: N88R, N88I, N88G, D20H, Q126L, Q126F, and C125S or C125A. "Medium molecular weight alginate," or "MMW-Alg" as used herein means an alginate with an approximate molecular weight of 75 kDa to 150 kDa.

"Polymer composition", as used herein, is a composition (e.g., a solution, mixture) comprising one or more polymers. As a class, "polymers' includes homopolymers, heteropolymers, co-polymers, block polymers, block co-polymers and can be both natural and synthetic. Homopolymers contain one type of building block, or monomer, whereas co-polymers contain more than one type of monomer.

"Polypeptide", as used herein, refers to a polymer comprising amino acid residues linked through peptide bonds and having at least 2, and in some embodiments, at least 3, 4, 5, 6, 7, 8, 9, 10, 12, 15, 20, 25, 30, 35, 40, 45, 50, 75, 100, 150 or 200 amino acid residues.

"Prevention," "prevent," and "preventing" as used herein refers to a treatment that comprises administering or applying a therapy, e.g., administering a composition of devices encapsulating cells (e.g., as described herein), prior to the onset of a disease, disorder, or condition to preclude the physical manifestation of said disease, disorder, or condition. In some embodiments, "prevention," "prevent," and "preventing" require that signs or symptoms of the disease, disorder, or condition have not yet developed or have not yet been observed. In some embodiments, treatment comprises prevention and in other embodiments it does not.

"Reference device", as used herein with respect to a claimed device (e.g., hydrogel capsule), means a device (e.g., hydrogel capsule) that: (i) lacks a particular feature, e.g., FBR-mitigating means (e.g., a barrier compartment comprising a small molecule compound, e.g., an afibrotic compound), (ii) encapsulates in the cell-containing compartment about the same quantity of cells of the same cell type(s) as in the claimed device, and (iii) has a substantially similar polymer composition and structure as in the claimed device other than lacking the particular feature (e.g., an afibrotic compound). In an embodiment, the number of live cells in the cell-containing compartment of a reference device is within 80% to 120%, or within 90% to 110%, of the number of live cells in the cell-containing compartment of the claimed device. In an embodiment, the cells in the reference and claimed devices are obtained from the same cell culture. In an embodiment, a substantially similar polymer composition means all polymers in the reference and claimed device, including the polymer component of any afibrotic polymer, as applicable, are of the same chemical and molecular weight class (e.g., an alginate with high G content and the same molecular weight range).

"Refractive index" as used herein refers to a dimensionless value representing the relative ratio of the speed of light in a medium (e.g., a sample) relative to the speed of light in a vacuum. The refractive index may be used to describe the phase velocity of light through the medium, e.g., how much the path of light is refracted when entering the medium (e.g., the sample). The refractive index of a sample may be measured by a refractometer and is temperature and wavelength dependent. Exemplary refractive indices include water (nD=1.333 at 20° C.) and ethanol (nD=1.36 at 20° C.).

"Sequence identity" or "percent identical", when used herein to refer to two nucleotide sequences or two amino acid sequences, means the two sequences are the same within a specified region, or have the same nucleotides or amino acids at a specified percentage of nucleotide or amino acid positions within the specified when the two sequences are compared and aligned for maximum correspondence over a comparison window or designated region. Sequence identity may be determined using standard techniques known in the art including, but not limited to, any of the algorithms described in US Patent Application Publication No. 2017/02334455. In an embodiment, the specified percentage of identical nucleotide or amino acid positions is at least about 80%, 85%, 90%, 91%, 92%, 93%, 94%, 95%, 96%, 97%, 98%, 99% or higher.

"Subject" as used herein refers to a human or non-human animal. In an embodiment, the subject is a human (i.e., a male or female), e.g., of any age group, a pediatric subject (e.g., infant, child, adolescent) or adult subject (e.g., young adult, middle-aged adult, or senior adult). In an embodiment, the subject is a non-human animal, for example, a mammal (e.g., a mouse, a dog, a primate (e.g., a cynomolgus monkey or a rhesus monkey)). In an embodiment, the subject is a commercially relevant mammal (e.g., a cattle, pig, horse, sheep, goat, cat, or dog) or a bird (e.g., a commercially relevant bird such as a chicken, duck, goose, or turkey). In certain embodiments, the animal is a mammal. The animal may be a male or female and at any stage of development. A non-human animal may be a transgenic animal.

"Treatment," "treat," and "treating" as used herein refers to one or more of reducing, reversing, alleviating, delaying the onset of, or inhibiting the progress of one or more of a symptom, manifestation, or underlying cause, of a disease, disorder, or condition. In an embodiment, treating comprises reducing, reversing, alleviating, delaying the onset of, or inhibiting the progress of a symptom of a disease, disorder, or condition. In an embodiment, treating comprises reducing, reversing, alleviating, delaying the onset of, or inhibiting the progress of a manifestation of a disease, disorder, or condition. In an embodiment, treating comprises reducing, reversing, alleviating, reducing, or delaying the onset of, an underlying cause of a disease, disorder, or condition. In some embodiments, "treatment," "treat," and "treating" require that signs or symptoms of the disease, disorder, or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., considering a history of symptoms and/or in light of genetic or other susceptibility factors). Treatment may also be continued after symptoms have resolved, for example, to delay or prevent recurrence. In some embodiments, treatment comprises prevention and in other embodiments it does not.

Selected Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and sub-range within the range. For example, "$C_1$-$C_6$ alkyl" is intended to encompass, $C_1$, $C_2$, $C_3$, $C_4$, $C_5$, $C_6$, $C_1$-$C_6$, $C_1$-$C_4$, $C_1$-$C_3$, $C_1$-$C_2$, $C_2$-$C_6$, $C_2$-$C_4$, $C_2$-$C_3$, $C_3$-$C_6$, $C_3$-$C_4$, $C_4$-$C_6$, $C_4$-$C_5$, and $C_5$-$C_6$ alkyl.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"), 1 to 10 carbon atoms ("$C_1$-$C_{12}$ alkyl"), 1 to 8 carbon atoms ("$C_1$-$C_8$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). In some embodiments, an alkyl group has 2 to 6 carbon atoms ("$C_2$-$C_6$alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 10 carbon atoms ("$C_2$-$C_{10}$ alkenyl"), 2 to 8 carbon atoms ("$C_2$-$C_6$ alkenyl"), 2 to 6 carbon atoms ("$C_2$-$C_6$ alkenyl"), 2 to 5 carbon atoms ("$C_2$-$C_5$ alkenyl"), 2 to 4 carbon atoms ("$C_2$-$C_4$ alkenyl"), 2 to 3 carbon atoms ("$C_2$-$C_3$ alkenyl"), or 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 10 carbon atoms ("$C_2$-$C_{10}$ alkynyl"), 2 to 8 carbon atoms ("$C_2$-$C_8$ alkynyl"), 2 to 6 carbon atoms ("$C_2$-$C_6$ alkynyl"), 2 to 5 carbon atoms ("$C_2$-$C_5$ alkynyl"), 2 to 4 carbon atoms ("$C_2$-$C_4$ alkynyl"), 2 to 3 carbon atoms ("$C_2$-$C_3$ alkynyl"), or 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent.

As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, and $—O—CH_2—CH_3$. Up to two or three heteroatoms may be consecutive, such as, for example, $—CH_2—NH—OCH_3$ and $—CH_2—O—Si(CH_3)_3$. Where "heteroalkyl" is recited, followed by recitations of specific heteroalkyl groups, such as $—CH_2O$, $—NR^CR^D$, or the like, it will be understood that the terms heteroalkyl and $—CH_2O$ or $—NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as $—CH_2O$, $—NR^CR^D$, or the like. Each instance of a heteroalkyl group may be independently optionally substituted, i.e., unsubstituted (an "unsubstituted heteroalkyl") or substituted (a "substituted heteroalkyl") with one or more substituents e.g., for instance from 1 to 5 substituents, 1 to 3 substituents, or 1 substituent.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. An alkylene, alkenylene, alkynylene, or heteroalkylene group may be described as, e.g., a $C_1$-$C_6$-membered alkylene, $C_2$-$C_6$-membered alkenylene, $C_2$-$C_6$-membered alkynylene, or $C_1$-$C_6$-membered heteroalkylene, wherein the term "membered" refers to the non-hydrogen atoms within the moiety. In the case of heteroalkylene groups, heteroatoms can also occupy either or both chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ may represent both $—C(O)_2R'—$ and $—R'C(O)_2—$.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, the terms “arylene” and “heteroarylene,” alone or as part of another substituent, mean a divalent radical derived from an aryl and heteroaryl, respectively.

As used herein, “cycloalkyl” refers to a radical of a non-aromatic cyclic hydrocarbon group having from 3 to 10 ring carbon atoms (“$C_3$-$C_{10}$ cycloalkyl”) and zero heteroatoms in the non-aromatic ring system. In some embodiments, a cycloalkyl group has 3 to 8 ring carbon atoms (“$C_3$-$C_8$cycloalkyl”), 3 to 6 ring carbon atoms (“$C_3$-$C_6$ cycloalkyl”), or 5 to 10 ring carbon atoms (“$C_5$-$C_{10}$ cycloalkyl”). A cycloalkyl group may be described as, e.g., a $C_4$-$C_7$-membered cycloalkyl, wherein the term “membered” refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_5$), cyclooctenyl ($C_5$), cubanyl ($C_5$), bicyclo[1.1.1]pentanyl ($C_5$), bicyclo[2.2.2]octanyl ($C_5$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro [4.5]decanyl ($C_{10}$), and the like. As the foregoing examples illustrate, in certain embodiments, the cycloalkyl group is either monocyclic (“monocyclic cycloalkyl”) or contain a fused, bridged or spiro ring system such as a bicyclic system (“bicyclic cycloalkyl”) and can be saturated or can be partially unsaturated. “Cycloalkyl” also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an “unsubstituted cycloalkyl”) or substituted (a “substituted cycloalkyl”) with one or more substituents.

“Heterocyclyl” as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon (“3-10 membered heterocyclyl”). In heterocyclyl groups that contain one or more nitrogen atoms, the point of attachment can be a carbon or nitrogen atom, as valency permits. A heterocyclyl group can either be monocyclic (“monocyclic heterocyclyl”) or a fused, bridged or Spiro ring system such as a bicyclic system (“bicyclic heterocyclyl”), and can be saturated or can be partially unsaturated. Heterocyclyl bicyclic ring systems can include one or more heteroatoms in one or both rings. “Heterocyclyl” also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term “membered” refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an “unsubstituted heterocyclyl”) or substituted (a “substituted heterocyclyl”) with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon (“5-10 membered heterocyclyl”). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur (“5-8 membered heterocyclyl”). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur (“5-6 membered heterocyclyl”). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, piperazinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl or thiomorpholinyl-1,1-dioxide. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Amino" as used herein refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, $C_4$-$C_{10}$ heterocyclyl, $C_6$-$C_{10}$ aryl, and $C_5$-$C_{10}$ heteroaryl. In some embodiments, amino refers to $NH_2$.

As used herein, "cyano" refers to the radical —CN.

As used herein, "halo" or "halogen," independently or as part of another substituent, mean, unless otherwise stated, a fluorine (F), chlorine (Cl), bromine (Br), or iodine (I) atom. As used herein, "hydroxy" refers to the radical —OH.

Alkyl, alkenyl, alkynyl, heteroalkyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present disclosure contemplates any and all such combinations to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds of Formula (I) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

Compounds of Formula (I) described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

The term "pharmaceutically acceptable salt" is meant to include salts of the active compounds that are prepared with relatively nontoxic acids or bases, depending on the particular substituents found on the compounds described herein. When compounds of Formula (I) used to prepare devices of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds used in the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al, *Journal of Pharmaceutical Science* 66: 1-19 (1977)). Certain specific compounds used in the devices of the present disclosure (e.g., a particle, a hydrogel capsule) contain both basic and acidic functionalities that allow the compounds to be converted into either base or acid addition salts. These salts may be prepared by methods known to those skilled in the art. Other pharmaceutically acceptable carriers known to those of skill in the art are suitable for use in the present disclosure.

Certain compounds of Formula (I) described herein can exist in unsolvated forms as well as solvated forms, including hydrated forms. In general, the solvated forms are equivalent to unsolvated forms and are encompassed within the scope of the present disclosure. Certain compounds of Formula (I) described herein may exist in multiple crystalline or amorphous forms. In general, all physical forms are equivalent for the uses contemplated by the present disclosure and are intended to be within the scope of the present disclosure.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound and wherein x is a number greater than 0.

The term "tautomer" as used herein refers to compounds that are interchangeable forms of a compound structure, and that vary in the displacement of hydrogen atoms and electrons. Thus, two structures may be in equilibrium through the movement of n electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

The symbol "∿∿∿" as used herein refers to a connection to an entity, e.g., a polymer (e.g., hydrogel-forming polymer such as alginate) or surface of an implantable device, e.g., a particle, a hydrogel capsule. The connection represented by "∿∿∿" may refer to direct attachment to the entity, e.g., a polymer or an implantable element, may refer to linkage to the entity through an attachment group. An "attachment group," as described herein, refers to a moiety for linkage of a compound of Formula (I) to an entity (e.g., a polymer or an implantable element (e.g., a device) as described herein), and may comprise any attachment chemistry known in the art. A listing of exemplary attachment groups is outlined in *Bioconjugate Techniques* ($3^{rd}$ ed, Greg T. Hermanson, Waltham, MA: Elsevier, Inc, 2013), which is incorporated herein by reference in its entirety. In some embodiments, an attachment group comprises alkyl, alkenyl, alkynyl, heteroalkyl, cycloalkyl, heterocyclyl, aryl, heteroaryl, —C(O)—, —OC(O)—, —N($R^C$)C(O)—, —C(O)N($R^C$)—, —N($R^C$)N($R^D$)—, —NCN—, —C(=N($R^C$)($R^D$))O—, —S—, —$S(O)_x$—, —$OS(O)_x$, —N($R^C$)$S(O)_x$—, —$S(O)_x$N($R^C$)—, —P($R^F$)$_y$—, —Si($OR^A$)$_2$—, —Si($R^G$)($OR^A$)—, —B($OR^A$)—, or a metal, wherein each of $R^A$, $R^C$, $R^D$, $R^F$, $R^G$, x and y is independently as described herein. In some embodiments, an attachment group comprises an amine, ketone, ester, amide, alkyl, alkenyl, alkynyl, or thiol. In some embodiments, an attachment group is a cross-linker. In some embodiments, the attachment group is —C(O)($C_1$-$C_6$-alkylene)-, wherein alkylene is substituted with $R^1$, and $R^1$ is as described herein. In some embodiments, the attachment group is —C(O)($C_1$-$C_6$-alkylene)-, wherein alkylene is substituted with 1-2 alkyl groups (e.g., 1-2 methyl groups). In some embodiments, the attachment group is —C(O)C($CH_3$)$_2$—. In some embodiments, the attachment group is —C(O)(methylene)-, wherein alkylene is substituted with 1-2 alkyl groups (e.g., 1-2 methyl groups). In some embodiments, the attachment group is —C(O)CH($CH_3$)—. In some embodiments, the attachment group is —C(O)C($CH_3$)—.

Features of Polymer Compositions

The present disclosure features methods of evaluating polymer compositions comprising at least one polymer modified with a small molecule compound. For example, using the methods described herein, the total concentration of a small molecule compound bound to the modified polymer(s) may be determined. The polymer compositions may be used to encapsulate cells (e.g., live cells) expressing a therapeutic agent, forming a semi-permeable device capable of releasing the therapeutic agent upon implant of the device into a subject, e.g., a human or other mammalian subject. The methods described herein may provide a means for reliably determining the concentration of a small molecule compound within the polymer composition, which may be useful, e.g., to gauge the stability of small molecule compound modification over time.

The small molecule compounds bound to the modified polymers in the polymer composition may comprise a naturally occurring small molecule or a non-naturally occurring small molecule, as well as variants thereof. In an embodiment, the small molecule compound comprises an alcohol, amine, carboxylic acid, ester, thiol, aryl, heteroaryl, ether, alkene, alkyne, azide, sulfonic acid, polyethylene glycol, or other moiety. The small molecule compound may be linked to the modified polymer in any manner, including through an amide linkage, ester linkage, thioester linkage, disulfide linkage, or ether linkage. In addition, a small molecule compound for use with the present disclosure may be modified in some way, e.g., via chemical or enzymatic modification (e.g., glycosylation, phosphorylation).

In some embodiments, the small molecule compound has an average molecular weight of 100 Da, 200 Da, 250 Da, 300 Da, 400 Da, 500 Da, 600 Da, 700 Da, 800 Da, 900 Da, 1 kDa, 1.5 kDa, 2 kDa, 2.5 kD, 5 kD, or greater. In some embodiments, the small molecule compound has an average molecular weight of 5 kDa, 2.5 kDa, 2 kDa, 1.5 kDa, 1 kDa, 900 Da, 800 Da, 700 Da, 600 Da, 500 Da, 400 Da, 300 Da, 250 Da, 200 Da, 150 Da, 100 Da, or less. In some embodiments, the small molecule compound has an average molecular weight of more than 100 Da. In some embodiments, the small molecule compound has an average molecular weight of more than 250 Da. In some embodiments, the small molecule compound has an average molecular weight of less than 500 Da. In some embodiments, the small molecule compound has an average molecular weight of less than 1 kDa. In some embodiments, the small molecule compound has an average molecular weight between 100 Da and 5 kDa, e.g., between 100 Da and 2.5 kDa, 100 Da and 2 kDa, 100 Da and 1 kDa, 200 Da and 5 kDa, 200 Da and 2.5 kDa, 200 Da and 2 kDa, 200 Da and 1 kDa, 250 Da and 5 kDa, 250 Da and 2.5 kDa, 250 Da and 2 kDa, 250 Da and 1 kDa, 500 Da and 5 kDa, 500 Da and 2.5 kDa, 500 Da and 2 kDa, or 500 Da and 1 kDa.

In some embodiments, the small molecule compound is an afibrotic compound. In an embodiment, the afibrotic compound is a compound of Formula (I):

(I)

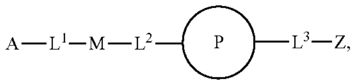

or a salt (e.g., pharmaceutically acceptable salt) thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —S(O)$_x$—, —N($R^C$)S(O)$_x$—, —S(O)$_x$N($R^C$)—, —P($R^F$)$_y$—, —Si($OR^A$)$_2$—, —Si($R^G$)($OR^A$)—, —B($OR^A$)—, or a metal, each of which is optionally linked to an attachment group (e.g., an attachment group described herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocycyl, or heteroaryl, each of which is optionally substituted by one or more $R^4$;

Z is hydrogen, alkyl, alkenyl, alkynyl, heteroalkyl, —$OR^A$, —C(O)$R^A$, —C(O)$OR^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), N($R^{C1}$)C(O)$R^{B1}$, C(O)N($R^{C1}$), $SR^{E1}$, S(O)$_x$$R^{E1}$, —OS(O)$_x$$R^{E1}$, —N($R^{C1}$)S(O)$_x$$R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, the small molecule compound of Formula (I) is a compound of Formula (I-a):

(I-a)

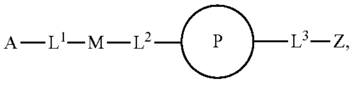

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, N($R^C$)C(O)($C_1$-$C_6$-alkylene)-, —N($R^C$)C(O)($C_1$-$C_6$-alkenylene)-, —NCN—, —C(=N($R^C$)($R^D$))O—, —S—, —S(O)$_x$—, —OS(O)$_x$—, —N($R^C$)S(O)$_x$—, —S(O)$_x$N($R^C$)—, —Si($OR^A$)$_2$—, —Si($R^G$)($OR^A$)—, —B($OR^A$)—, or a metal, each of which is optionally linked to an attachment group (e.g., an attachment group described herein) and optionally substituted by one or more R';

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), N($R^{C1}$)C(O)$R^{B1}$, C(O)N($R^{C1}$), $SR^{E1}$, $S(O)_xR^{E1}$, $—OS(O)_xR^{E1}$, $—N(R^{C1})S(O)_xR^{E1}$, $—S(O)_xN(R^{C1})(R^{D1})$, $—P(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, for Formulas (I) and (I-a), A is alkyl, alkenyl, alkynyl, heteroalkyl, cycloalkyl, heterocyclyl, aryl, heteroaryl, —O—, —C(O)O—, —C(O)—, —OC(O)—$N(R^C)C(O)$—, —$N(R^C)C(O)(C_1$-$C_6$-alkylene)-, —$N(R^C)C(O)(C_1$-$C_6$-alkenylene)-, or —$N(R^C)$—. In some embodiments, A is alkyl, alkenyl, alkynyl, heteroalkyl, cycloalkyl, heterocyclyl, aryl, heteroaryl, —O—, —C(O)O—, —C(O)—, —OC(O)—, or —$N(R^C)$—. In some embodiments, A is alkyl, alkenyl, alkynyl, heteroalkyl, —O—, —C(O)O—, —C(O)—, —OC(O)—, or —$N(R^C)$—. In some embodiments, A is alkyl, —O—, —C(O)O—, —C(O)—, —OC(O), or —$N(R^C)$—. In some embodiments, A is —$N(R^C)C(O)$—, —$N(R^C)C(O)(C_1$-$C_6$-alkylene)-, or —$N(R^C)C(O)(C_1$-$C_6$-alkenylene)-. In some embodiments, A is —$N(R^C)$—. In some embodiments, A is —$N(R^C)$—, and $R^C$ an $R^D$ is independently hydrogen or alkyl. In some embodiments, A is —NH—. In some embodiments, A is —$N(R^C)C(O)(C_1$-$C_6$-alkylene)-, wherein alkylene is substituted with $R^1$. In some embodiments, A is —$N(R^C)C(O)(C_1$-$C_6$-alkylene)-, and is alkyl (e.g., methyl). In some embodiments, A is —$NHC(O)C(CH_3)_2$—. In some embodiments, A is —$N(R^C)C(O)$(methylene)-, and R' is alkyl (e.g., methyl). In some embodiments, A is —$NHC(O)CH(CH_3)$—. In some embodiments, A is —$NHC(O)C(CH_3)$—.

In some embodiments, for Formulas (I) and (I-a), $L^1$ is a bond, alkyl, or heteroalkyl. In some embodiments, $L^1$ is a bond or alkyl. In some embodiments, $L^1$ is a bond. In some embodiments, $L^1$ is alkyl. In some embodiments, $L^1$ is $C_1$-$C_6$ alkyl. In some embodiments, $L^1$ is —$CH_2$—, —$CH(CH_3)$—, —$CH_2CH_2CH_2$, or —$CH_2CH_2$—. In some embodiments, $L^1$ is —$CH_2$— or —$CH_2CH_2$—.

In some embodiments, for Formulas (I) and (I-a), $L^3$ is a bond, alkyl, or heteroalkyl. In some embodiments, $L^3$ is a bond. In some embodiments, $L^3$ is alkyl. In some embodiments, $L^3$ is $C_1$-$C_{12}$ alkyl. In some embodiments, $L^3$ is $C_1$-$C_6$ alkyl. In some embodiments, $L^3$ is —$CH_2$—. In some embodiments, $L^3$ is heteroalkyl. In some embodiments, $L^3$ is $C_1$-$C_{12}$ heteroalkyl, optionally substituted with one or more $R^2$ (e.g., oxo). In some embodiments, $L^3$ is $C_1$-$C_6$ heteroalkyl, optionally substituted with one or more $R^2$ (e.g., oxo). In some embodiments, $L^3$ is —$C(O)OCH_2$—, —$CH_2(OCH_2CH_2)_2$—, —$CH_2(OCH_2CH_2)_3$—, $CH_2CH_2O$—, or —$CH_2O$—. In some embodiments, $L^3$ is —$CH_2O$—.

In some embodiments, for Formulas (I) and (I-a), M is absent, alkyl, heteroalkyl, aryl, or heteroaryl. In some embodiments, M is heteroalkyl, aryl, or heteroaryl. In some embodiments, M is absent. In some embodiments, M is alkyl (e.g., $C_1$-$C_6$ alkyl). In some embodiments, M is —$CH_2$—. In some embodiments, M is heteroalkyl (e.g., $C_1$-$C_6$ heteroalkyl). In some embodiments, M is $(—OCH_2CH_2—)z$, wherein z is an integer selected from 1 to 10. In some embodiments, z is an integer selected from 1 to 5. In some embodiments, M is —$OCH_2CH_2$—, $(—OCH_2CH_2—)z$, $(—OCH_2CH_2—)_3$, $(—OCH_2CH_2—)_4$, or $(—OCH_2CH_2—)_5$. In some embodiments, M is —$OCH_2CH_2$—, $(—OCH_2CH_2—)_2$, $(—OCH_2CH_2—)_3$, or $(—OCH_2CH_2—)_4$. In some embodiments, M is $(—OCH_2CH_2—)_3$. In some embodiments, M is aryl. In some embodiments, M is phenyl. In some embodiments, M is unsubstituted phenyl. In some embodiments, M is

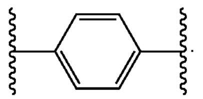

In some embodiments, M is phenyl substituted with $R^7$ (e.g., 1 $R^7$). In some embodiments, M is

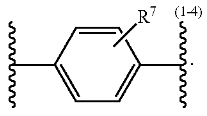

In some embodiments, $R^7$ is $CF_3$.

In some embodiments, for Formulas (I) and (I-a), P is absent, heterocyclyl, or heteroaryl. In some embodiments, P is absent. In some embodiments, for Formulas (I) and (I-a), P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is imidazolyl. In some embodiments, P is

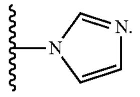

In some embodiments, P is triazolyl. In some embodiments, P is 1,2,3-triazolyl. In some embodiments, P is

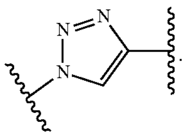 [SMILES: *c1cn(*)nn1]

In some embodiments, P is heterocyclyl. In some embodiments, P is a 5-membered heterocyclyl or a 6-membered heterocyclyl. In some embodiments, P is imidazolidinonyl. In some embodiments, P is

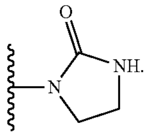 [SMILES: *N1CCNC1=O]

In some embodiments, P is thiomorpholinyl-1,1-dioxidyl.

In some embodiments, P is

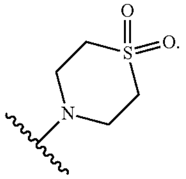 [SMILES: *N1CCS(=O)(=O)CC1]

In some embodiments, for Formulas (I) and (I-a), Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 4-membered heterocyclyl, 5-membered heterocyclyl, or 6-membered heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is

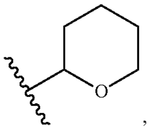 , 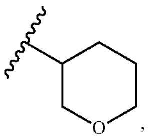 , or 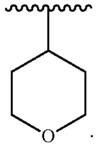 .

In some embodiments, Z is a 4-membered oxygen-containing heterocyclyl. In some embodiments, Z is

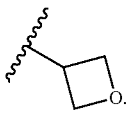 [SMILES: *C1COC1]

In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1,1-dioxidyl. In some embodiments, Z is

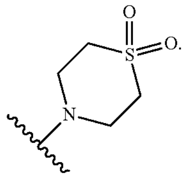 [SMILES: *N1CCS(=O)(=O)CC1]

In some embodiments, Z is a nitrogen-containing heterocyclyl. In some embodiments, Z is a 6-membered nitrogen-containing heterocyclyl. In some embodiments, Z is

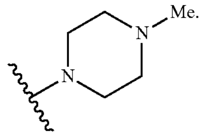 [SMILES: *N1CCN(C)CC1]

In some embodiments, Z is a bicyclic heterocyclyl. In some embodiments, Z is a bicyclic nitrogen-containing heterocyclyl, optionally substituted with one or more $R^5$. In some embodiments, Z is 2-oxa-7-azaspiro[3.5]nonanyl. In some embodiments, Z is

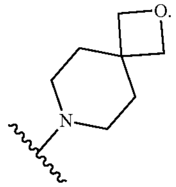 [SMILES: *N1CCC2(CC1)COC2]

In some embodiments, Z is 1-oxa-3,8-diazaspiro[4.5]decan-2-one. In some embodiments, Z is

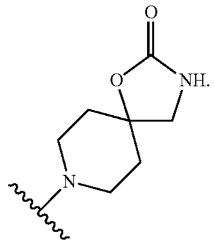 [SMILES: *N1CCC2(CC1)CNC(=O)O2]

In some embodiments, for Formulas (I) and (I-a), Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, for Formulas (I) and (I-a), Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl.

In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, $C(O)R^{B1}$, or —$N(R^{C1})(R^{D1})$. In some embodiments, Z is $C_1$-$C_8$ alkyl substituted with 1 $R^5$, wherein $R^5$ is —$OR^{A1}$ or —$C(O)OR^{A1}$. In some embodiments, Z is $C_1$-$C_8$ alkyl substituted with 1 $R^5$, wherein $R^5$ is —$OR^{A1}$ or —C(O)OH. In some embodiments, Z is —$CH_3$.

In some embodiments, for Formulas (I) and (I-a), Z is heteroalkyl. In some embodiments, Z is $C_1$-$C_{12}$ heteroalkyl. In some embodiments, Z is $C_1$-$C_{10}$ heteroalkyl. In some embodiments, Z is $C_1$-$C_8$ heteroalkyl. In some embodiments, Z is $C_1$-$C_6$ heteroalkyl. In some embodiments, Z is a nitrogen-containing heteroalkyl optionally substituted with one or more $R^5$. In some embodiments, Z is a nitrogen and sulfur-containing heteroalkyl substituted with 1-5 $R^5$. In some embodiments, Z is N-methyl-2-(methylsulfonyl)ethan-1-aminyl.

In some embodiments, Z is —$OR^A$ or —$C(O)OR^A$. In some embodiments, Z is —$OR^A$ (e.g., —OH or —$OCH_3$). In some embodiments, Z is —$OCH_3$. In some embodiments, Z is —$C(O)OR^A$ (e.g., —C(O)OH).

In some embodiments, Z is hydrogen.

In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound of Formula (I) is a compound of Formula (I-b):

(I-b)

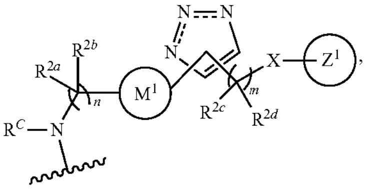

or a pharmaceutically acceptable salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is absent, $N(R^{10})(R^{11})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —$C(O)OR^{A1}$, —$C(O)R^{B1}$, —$OC(O)R^{B1}$, —$C(O)N(R^{C1})$, cycloalkyl, heterocyclyl, aryl, or heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 1, 2, 3, 4, 5, or 6; and "〰" refers to a connection to an attachment group or a polymer described herein. In some embodiments, for each $R^3$ and $R^5$, each alkyl, alkenyl, alkynyl, heteroalkyl, cycloalkyl, heterocyclyl, aryl, or heteroaryl is optionally and independently substituted with halogen, oxo, cyano, cycloalkyl, or heterocyclyl.

In some embodiments, the compound of Formula (I-b) is a compound of Formula (I-b-i):

(I-b-i)

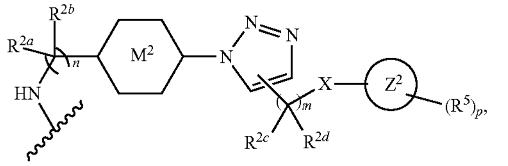

or a pharmaceutically acceptable salt thereof, wherein Ring $M^2$ is aryl or heteroaryl optionally substituted with one or more $R^3$; Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; X is absent, O, or S; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; or two $R^5$ are taken together to form a 5-6 membered ring fused to Ring $Z^2$; each $R^{A1}$ and $R^{B1}$ is independently hydrogen, alkyl, or heteroalkyl; m and n are each independently 1, 2, 3, 4, 5, or 6; p is 0, 1, 2, 3, 4, 5, or 6; and "〰" refers to a connection to an attachment group or a polymer described herein.

In some embodiments, the compound of Formula (I-b-i) is a compound of Formula (I-b-ii):

(I-b-ii)

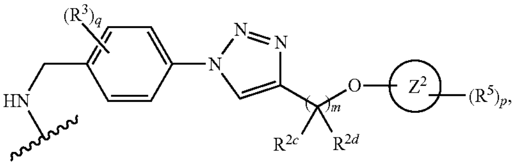

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ and taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl;

each of p and q is independently 0, 1, 2, 3, 4, 5, or 6; and “∼∼∼ ” refers to a connection to an attachment group or a polymer described herein.

In some embodiments, the compound of Formula (I) is a compound of Formula (I-c):

(I-c)

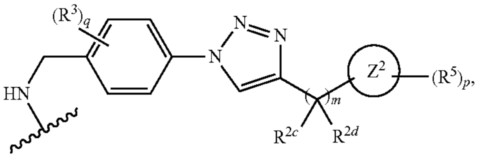

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ is taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; m is 1, 2, 3, 4, 5, or 6; each of p and q is independently 0, 1, 2, 3, 4, 5, or 6; and “∼∼∼ ” refers to a connection to an attachment group or a polymer described herein.

In some embodiments, the compound of Formula (I) is a compound of Formula (I-d):

(I-d)

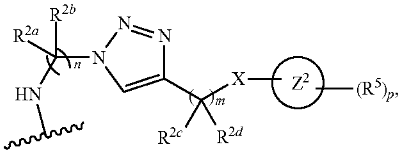

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and “∼∼∼ ” refers to a connection to an attachment group or a polymer described herein.

In some embodiments, the compound of Formula (I) is a compound of Formula (I-e):

(I-e)

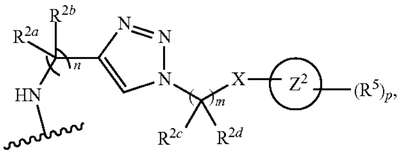

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$C(O)OR^{A1}$, or —$C(O)R^{B1}$; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and “∼∼∼ ” refers to a connection to an attachment group or a polymer described herein.

In some embodiments, the compound of Formula (I) is a compound of Formula (I-f):

(I-f)

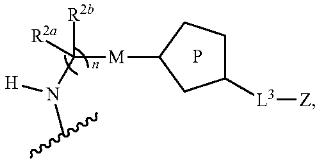

or a pharmaceutically acceptable salt thereof, wherein M is alkyl optionally substituted with one or more $R^3$; Ring P is heteroaryl optionally substituted with one or more $R^4$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^4$, and $R^5$ is independently alkyl, heteroalkyl, halogen, oxo, —$OR^{A1}$, $C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and “∼∼∼ ” refers to a connection to an attachment group or a polymer described herein.

In some embodiments, the compound of Formula (I) is a compound of Formula (II):

(II)

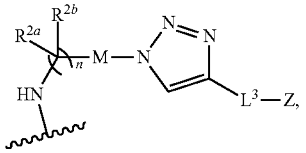

or a pharmaceutically acceptable salt thereof, wherein M is a bond, alkyl or aryl, wherein alkyl and aryl is optionally substituted with one or more $R^3$; $L^3$ is alkyl or heteroalkyl optionally substituted with one or more $R^2$; Z is hydrogen, alkyl, heteroalkyl, cycloalkyl, heterocyclyl, aryl, heteroaryl or —$OR^A$, wherein alkyl, heteroalkyl, cycloalkyl, heterocyclyl, aryl, and heteroaryl is optionally substituted with one or more $R^5$; $R^A$ is hydrogen; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and “∼∼∼ ” refers to a connection to an attachment group or a polymer described herein.

In some embodiments, the compound of Formula (II) is a compound of Formula (II-a):

(II-a)

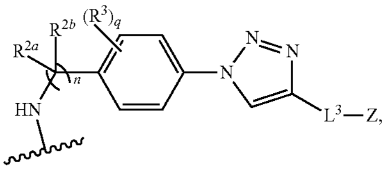

or a pharmaceutically acceptable salt thereof, wherein $L^3$ is alkyl or heteroalkyl, each of which is optionally substituted with one or more $R^2$; Z is hydrogen, alkyl, heteroalkyl, or —$OR^A$, wherein alkyl and heteroalkyl are optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, $C(O)OR^{A1}$, or —$C(O)R^{B1}$; $R^A$ is hydrogen; each $R^{A1}$ and $R^{B1}$ is independently hydrogen, alkyl, or heteroalkyl; n is independently 1, 2, 3, 4, 5, or 6; and "∿∿" refers to a connection to an attachment group or a polymer described herein.

In some embodiments, the compound of Formula (I) is a compound of Formula (III):

(III)

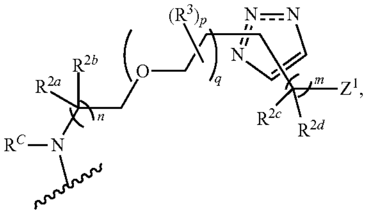

or a pharmaceutically acceptable salt thereof, wherein $Z^1$ is alkyl, alkenyl, alkynyl, heteroalkyl, cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, or heteroalkyl, wherein each of alkyl, alkenyl, alkynyl, or heteroalkyl is optionally substituted with 1-6 $R^6$; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; q is an integer from 0 to 25; "∿∿" and refers to a connection to an attachment group or a polymer described herein.

In some embodiments, the compound of Formula (III) is a compound of Formula (III-a):

(III-a)

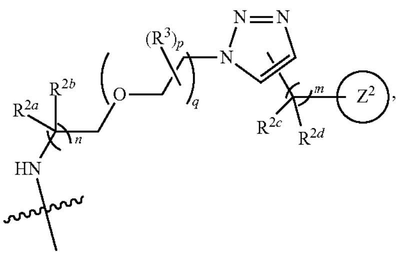

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)R^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "∿∿" refers to a connection to an attachment group or a polymer described herein.

In some embodiments, the compound of Formula (III-a) is a compound of Formula (III-b):

(III-b)

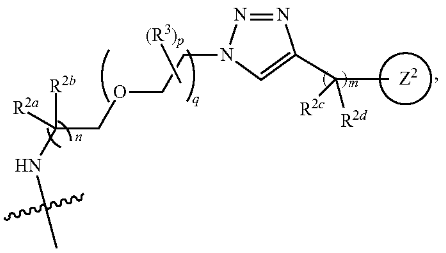

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "∿∿" refers to a connection to an attachment group or a polymer described herein.

In some embodiments, the compound of Formula (III-a) is a compound of Formula (III-c):

(III-c)

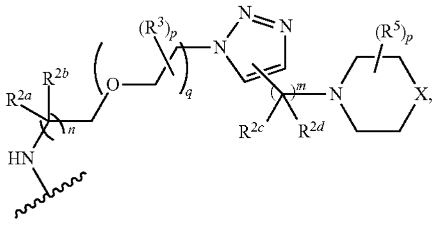

or a pharmaceutically acceptable salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and "∿∿∿ " refers to a connection to an attachment group or a polymer described herein.

In some embodiments, the compound of Formula (III-c) is a compound of Formula (III-d):

(III-d)

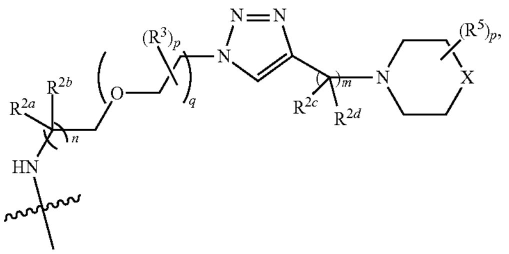

or a pharmaceutically acceptable salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and "∿∿∿ " refers to a connection to an attachment group or a polymer described herein.

In some embodiments, the compound is a compound of Formula (I). In some embodiments, $L^2$ is a bond and P and $L^3$ are independently absent.

In some embodiments, the compound is a compound of Formula (I-a). In some embodiments of Formula (II-a), $L^2$ is a bond, P is heteroaryl, $L^3$ is a bond, and Z is hydrogen. In some embodiments, P is heteroaryl, $L^3$ is heteroalkyl, and Z is alkyl. In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound is a compound of Formula (I-b). In some embodiments, P is absent, $L^1$ is —$NHCH_2$, $L^2$ is a bond, M is aryl (e.g., phenyl), $L^3$ is —$CH_2O$, and Z is heterocyclyl (e.g., a nitrogen-containing heterocyclyl, e.g., thiomorpholinyl-1,1-dioxide). In some embodiments, the compound of Formula (I-b) is Compound 116.

In some embodiments of Formula (I-b), P is absent, $L^1$ is —$NHCH_2$, $L^2$ is a bond, M is absent, $L^3$ is a bond, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-b) is Compound 105.

In some embodiments, the compound is a compound of Formula (I-b-i). In some embodiments of Formula (I-b-i), each of $R^{2a}$ and $R^{2b}$ is independently hydrogen or $CH_3$, each of $R^{2c}$ and $R^{2d}$ is independently hydrogen, m is 1 or 2, n is 1, X is O, p is 0, $M^2$ is phenyl optionally substituted with one or more $R^3$, $R^3$ is —$CF_3$, and $Z^2$ is heterocyclyl (e.g., an oxygen-containing heterocyclyl, e.g., tetrahydropyranyl, tetrahydrofuranyl, oxetanyl, or oxiranyl). In some embodiments, the compound of Formula (I-b-i) is Compound 100, Compound 106, Compound 107, Compound 108, Compound 109, or Compound 111.

In some embodiments, the compound is a compound of Formula (I-b-ii). In some embodiments of Formula (I-b-ii), each of $R^{2a}$, $R^{2b}$, $R^{2c}$, and $R^{2d}$ is independently hydrogen, q is 0, p is 0, m is 1, and $Z^2$ is heterocyclyl (e.g., an oxygen-containing heterocyclyl, e.g., tetrahydropyranyl). In some embodiments, the compound of Formula (I-b-ii) is Compound 100.

In some embodiments, the compound is a compound of Formula (I-c). In some embodiments of Formula (I-c), each of $R^{2c}$ and $R^{2d}$ is independently hydrogen, m is 1, p is 1, q is 0, $R^5$ is —$CH_3$, and Z is heterocyclyl (e.g., a nitrogen-containing heterocyclyl, e.g., piperazinyl).

In some embodiments, the compound of Formula (I-c) is Compound 113.

In some embodiments, the compound is a compound of Formula (I-d). In some embodiments of Formula (I-d), each of $R^{2a}$, $R^{2b}$, $R^{2c}$, and $R^{2d}$ is independently hydrogen, m is 1, n is 3, X is O, p is 0, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-d) is Compound 110 or Compound 114.

In some embodiments, the compound is a compound of Formula (I-f). In some embodiments of Formula (I-f), each of $R^{2a}$ and $R^{2b}$ is independently hydrogen, n is 1, M is —$CH_2$—, P is a nitrogen-containing heteroaryl (e.g., imidazolyl), $L^3$ is —$C(O)OCH_2$—, and Z is $CH_3$. In some embodiments, the compound of Formula (I-f) is Compound 115.

In some embodiments, the compound is a compound of Formula (II-a). In some embodiments of Formula (II-a), each of $R^{2a}$ and $R^{2b}$ is independently hydrogen, n is 1, q is 0, $L^3$ is —$CH_2(OCH_2CH_2)_2$, and Z is —$OCH_3$. In some embodiments, the compound of Formula (II-a) is Compound 112.

In some embodiments of Formula (II-a), each of $R^{2a}$ and $R^{2b}$ is independently hydrogen, n is 1, $L^3$ is a bond or —$CH_2$, and Z is hydrogen or —OH. In some embodiments, the compound of Formula (II-a) is Compound 103 or Compound 104.

In some embodiments, the compound is a compound of Formula (III). In some embodiments of Formula (III), each of $R^{2a}$, $R^{2b}$, $R^{2c}$, and $R^{2d}$ is independently hydrogen, m is 1, n is 2, q is 3, p is 0, $R^C$ is hydrogen, and $Z^1$ is heteroalkyl optionally substituted with $R^5$ (e.g., —$N(CH_3)(CH_2CH_2)S(O)_2CH_3$). In some embodiments, the compound of Formula (III) is Compound 120.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 0, n is 2, q is 3, p is 0, and $Z^2$ is aryl (e.g., phenyl) substituted with 1 $R^5$ (e.g., —$NH_2$). In some embodiments, the compound of Formula (III-b) is Compound 102.

In some embodiments, the compound is a compound of Formula (III-b). In some embodiments of Formula (III-b), each of $R^{2a}$, $R^{2b}$, $R^{2c}$ and $R^{2d}$ is independently hydrogen, m is 1, n is 2, q is 3, p is 0, $R^C$ is hydrogen, and $Z^2$ is heterocyclyl (e.g., an nitrogen-containing heterocyclyl, e.g., a nitrogen-containing spiro heterocyclyl, e.g., 2-oxa-7-azaspiro[3.5]nonanyl). In some embodiments, the compound of Formula (III-b) is Compound 121.

In some embodiments, the compound is a compound of Formula (III-d). In some embodiments of Formula (III-d), each of $R^{2a}$, $R^{2b}$, $R^{2c}$, and $R^{2d}$ is independently hydrogen, m is 1, n is 2, q is 1, 2, 3, or 4, p is 0, and X is $S(O)_2$. In some embodiments of Formula (III-d), each of $R^{2a}$ and $R^{2b}$ is independently hydrogen, m is 1, n is 2, q is 1, 2, 3, or 4, p is 0, and X is $S(O)_2$. In some embodiments, the compound of Formula (III-d) is Compound 101, Compound 117, Compound 118, or Compound 119.

In some embodiments, the compound is a compound of Formula (I-b), (I-d), or (I-e). In some embodiments, the compound is a compound of Formula (I-b), (I-d), or (II). In some embodiments, the compound is a compound of Formula (I-b), (I-d), or (I-f). In some embodiments, the compound is a compound of Formula (I-b), (I-d), or (III).

In some embodiments, the compound of Formula (I) is not a compound disclosed in WO2012/112982, WO2012/167223, WO2014/153126, WO2016/019391, WO 2017/075630. In an embodiment, the compound of Formula (I) is a compound disclosed in any one of WO 2018/067615 and WO2019/169333, each of which is incorporated herein by reference in its entirety.

In some embodiments, the afibrotic compound (e.g., a compound of Formula (I)) comprises a compound shown in Table 1, or a pharmaceutically acceptable salt thereof.

TABLE 1

| Exemplary small molecule compounds | |
|---|---|
| Compound No. | Structure |
| 100 | 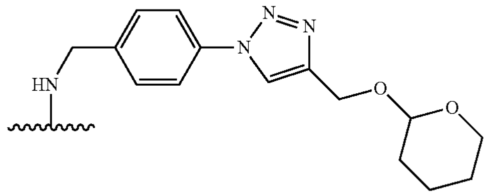 [SMILES: *NCc1ccc(-n2cc(COC3CCCCO3)nn2)cc1] |
| 101 | 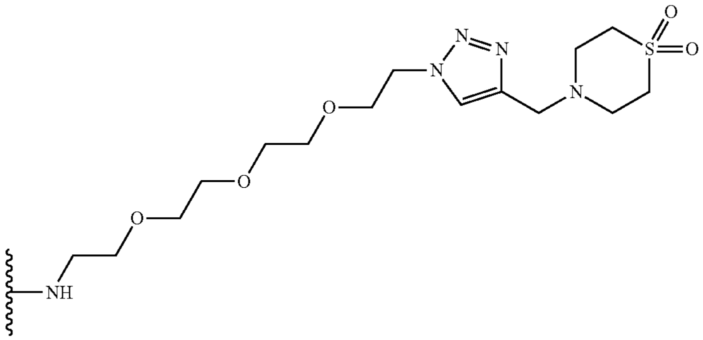 [SMILES: *NCCOCCOCCOCCn1cc(CN2CCS(=O)(=O)CC2)nn1] |
| 102 | 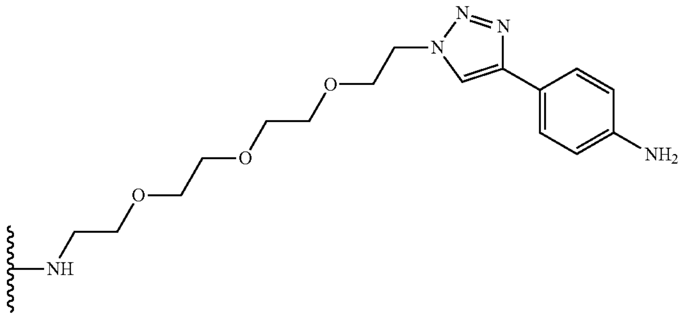 [SMILES: *NCCOCCOCCOCCn1cc(-c2ccc(N)cc2)nn1] |

TABLE 1-continued
| Exemplary small molecule compounds | |
|---|---|
| Compound No. | Structure |
| 103 | 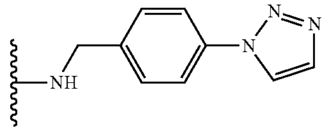 [SMILES: *NCc1ccc(-n2ccnn2)cc1] |
| 104 | 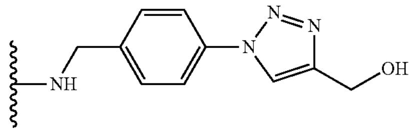 [SMILES: *NCc1ccc(-n2cc(CO)nn2)cc1] |
| 105 | 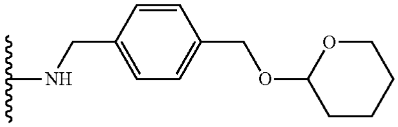 [SMILES: *NCc1ccc(COC2CCCCO2)cc1] |
| 106 | 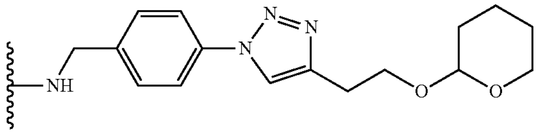 [SMILES: *NCc1ccc(-n2cc(CCOC3CCCCO3)nn2)cc1] |
| 107 | 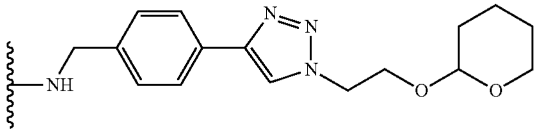 [SMILES: *NCc1ccc(-c2cn(CCOC3CCCCO3)nn2)cc1] |
| 108 | 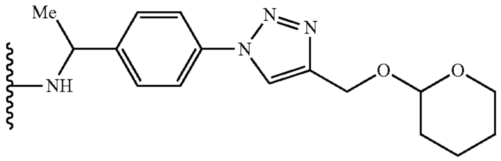 [SMILES: *NC(C)c1ccc(-n2cc(COC3CCCCO3)nn2)cc1] |
| 109 | 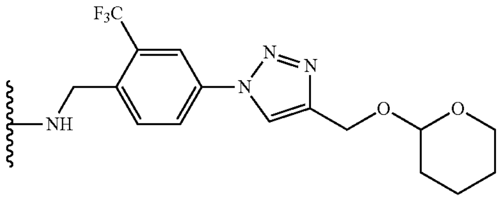 [SMILES: *NCc1ccc(-n2cc(COC3CCCCO3)nn2)cc1C(F)(F)F] |
| 110 | 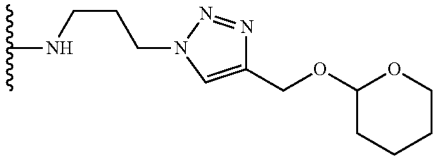 [SMILES: *NCCCn1cc(COC2CCCCO2)nn1] |
| 111 | 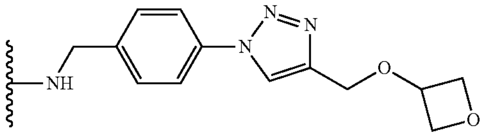 [SMILES: *NCc1ccc(-n2cc(COC3COC3)nn2)cc1] |

TABLE 1-continued
| Exemplary small molecule compounds | |
|---|---|
| Compound No. | Structure |
| 112 | 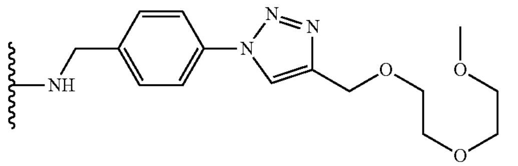 [SMILES: *NCc1ccc(-n2cc(COCCOCCOC)nn2)cc1] |
| 113 | 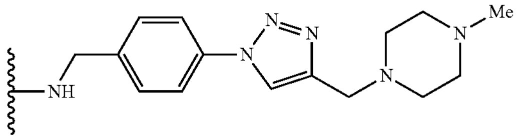 [SMILES: *NCc1ccc(-n2cc(CN3CCN(C)CC3)nn2)cc1] |
| 114 | 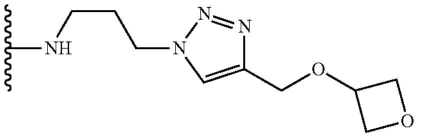 [SMILES: *NCCCn1cc(COC2COC2)nn1] |
| 115 | 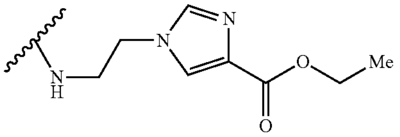 [SMILES: *NCCn1cnc(C(=O)OCC)c1] |
| 116 | 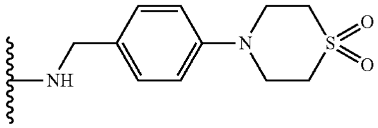 [SMILES: *NCc1ccc(N2CCS(=O)(=O)CC2)cc1] |
| 117 | 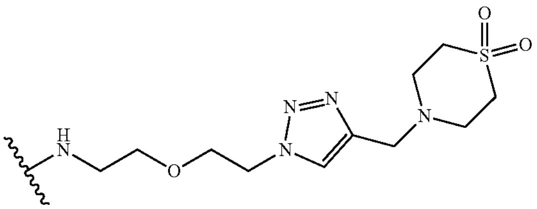 [SMILES: *NCCOCCn1cc(CN2CCS(=O)(=O)CC2)nn1] |
| 118 | 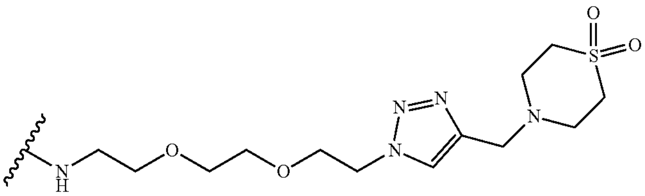 [SMILES: *NCCOCCOCCn1cc(CN2CCS(=O)(=O)CC2)nn1] |
| 119 | 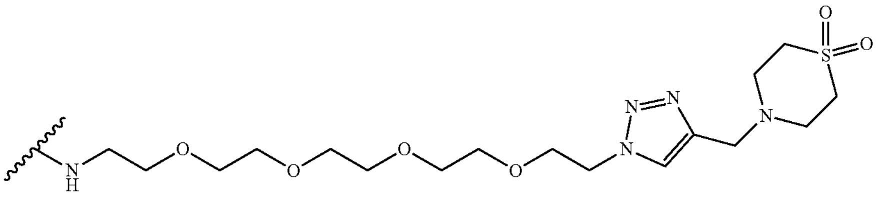 [SMILES: *NCCOCCOCCOCCOCCn1cc(CN2CCS(=O)(=O)CC2)nn1] |
| 120 | 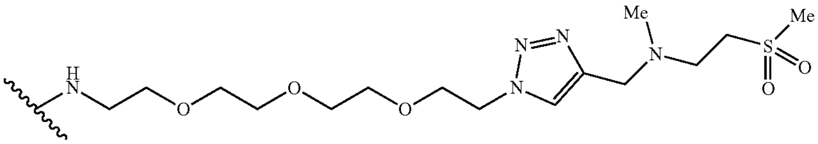 [SMILES: *NCCOCCOCCOCCn1cc(CN(C)CCS(C)(=O)=O)nn1] |

TABLE 1-continued

| Exemplary small molecule compounds | |
|---|---|
| Compound No. | Structure |
| 121 | 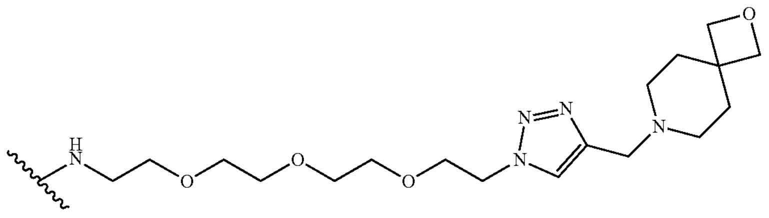 [SMILES: *NCCOCCOCCOCCn1cc(CN2CCC3(CC2)COC3)nn1] |

In some embodiments, the small molecule compound bound to a modified polymer is a compound of Formula (I) (e.g., Formulas (I-a), (I-b), (I-c), (I-d), (I-e), (II), (II-a), (III), (III-a), (III-b), (III-c), or (III-d)), or a pharmaceutically acceptable salt thereof and is selected from:

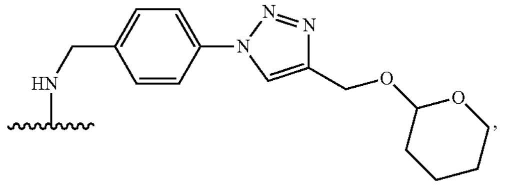

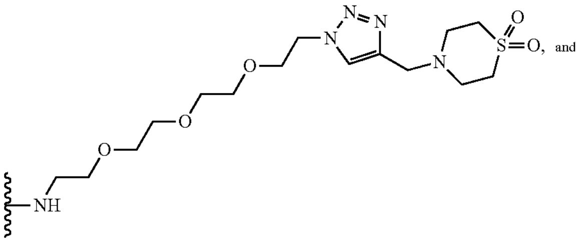

and

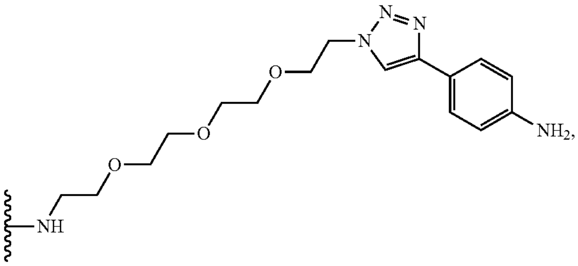

or a pharmaceutically acceptable salt thereof.

In some embodiments, the modified polymer described herein comprises the compound of

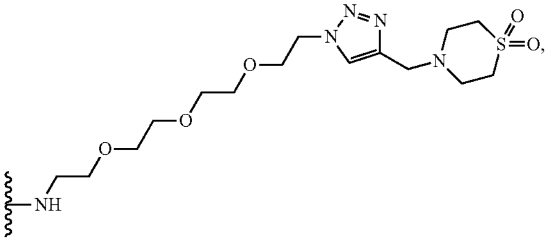

-continued

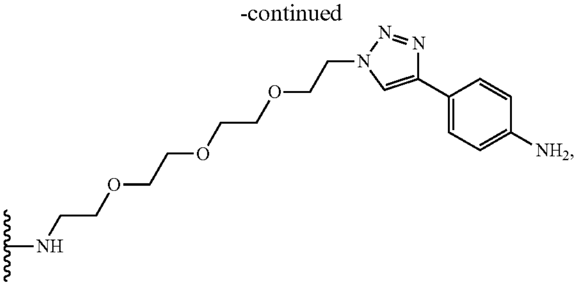

or a pharmaceutically acceptable salt of either compound.

Each small molecule compound (e.g., afibrotic compound) may be is attached to a polymer in the polymer composition via an attachment group. The attachment group may comprise an alkyl, carbonyl, amide, ester, thioester, disulfide bond, alkene, or other moiety. In some embodiments, the attachment group is —$C(O)(C_1$-$C_6$-alkylene)-, wherein alkylene is substituted with and $R^1$ is as described herein. In some embodiments, the attachment group is —$C(O)(C_1$-$C_6$-alkylene)-, wherein alkylene is substituted with 1-2 alkyl groups (e.g., 1-2 methyl groups). In some embodiments, the attachment group is —$C(O)C(CH_3)_2$—. In some embodiments, the attachment group is —C(O)(methylene)-, wherein alkylene is substituted with 1-2 alkyl groups (e.g., 1-2 methyl groups). In some embodiments, the attachment group is —$C(O)CH(CH_3)$—. In some embodiments, the attachment group is —$C(O)C(CH_3)$—

In an embodiment, the polymer composition comprises a single polymer modified with a small molecule compound. In another embodiment, the polymer composition comprises a plurality of polymers modified with a small molecule compound, e.g., at least 2 modified polymers, at least 3 modified polymers, or at least 4 modified polymers. The polymer compositions may comprise a plurality of polymers modified with the same small molecule compound, or a plurality of polymers modified with different small molecule compounds. The polymer compositions may comprise a mixture of modified polymers and unmodified polymers.

In an embodiment, the polymer composition comprises a first modified polymer, e.g., modified with a compound of Formula (I) (e.g., a compound described in Table 1) or a pharmaceutically acceptable salt thereof. In another embodiment, the polymer composition comprises a second modified polymer, e.g., compound of Formula (I) (e.g., a compound described in Table 1) or a pharmaceutically acceptable salt thereof.

Each of the modified and unmodified polymers in the polymer composition may be a linear, branched, or cross-linked polymer, or a polymer of selected molecular weight ranges, degree of polymerization, viscosity or melt flow rate. Exemplary polymers within the polymer composition include naturally occurring polymers and non-naturally occurring polymers (e.g., synthetic polymers). For example, the polymer composition may include polystyrene, polyethylene, polypropylene, polyacetylene, poly(vinyl chloride) (PVC), polyvinyl alcohol (PVA), polyolefin copolymers, poly(urethane)s, polyacrylates and polymethacrylates, polyacrylamides and polymethacrylamides, poly(methyl methacrylate), poly(2-hydroxyethyl methacrylate), polyesters, polysiloxanes, polydimethylsiloxane (PDMS), polyethers, poly(orthoester), poly(carbonates), poly(hydroxyalkanoate)s, polyfluorocarbons, PEEK®, Teflon® (polytetrafluoroethylene, PTFE), PEEK, silicones, epoxy resins, Kevlar®, Dacron® (a condensation polymer obtained from ethylene glycol and terephthalic acid), polyethylene glycol, nylon, polyalkenes, phenolic resins, natural and synthetic elastomers, adhesives and sealants, polyolefins, polysulfones, polyacrylonitrile, biopolymers such as polysaccharides and natural latex, collagen, cellulosic polymers (e.g., alkyl celluloses, etc.), polyethylene glycol and 2-hydroxyethyl methacrylate (HEMA), polysaccharides, poly(glycolic acid), poly(L-lactic acid) (PLLA), poly(lactic glycolic acid) (PLGA), a polydioxanone (PDA), racemic poly(lactic acid), polycarbonates, (e.g., polyamides (e.g., nylon)), fluoroplastics, carbon fiber, agarose, alginate, chitosan, and blends or copolymers thereof. Branched polymers can include one or more of the following types: star polymers, comb polymers, brush polymers, dendronized polymers, ladders, and dendrimers. A polymer may be a thermoresponsive polymer, e.g., gel (e.g., becomes a solid or liquid upon exposure to heat or a certain temperature) or a photocrosslinkable polymer. The amount of a modified polymer in the polymer composition (e.g., by % weight of the polymer composition, actual weight of the polymer) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In an embodiment, the polymer composition may comprise a polymer selected from alginate, chitosan, hyaluronate, a polyethylene glycol (PEG), a polyacrylamide, gelatin, poly(L-lactic acid) (PLLA), poly(lactic glycolic acid) (PLGA), carboxymethylcellulose, and carboxymethylchitosan. In an embodiment, the polymer composition does not comprise a polyamide polymer. In addition to the polymers described herein, the polymer composition may contain one or more unmodified naturally-occurring or synthetic polymers of any of the above-recited polymer classes to help provide structural integrity to the semi-permeable device and/or help provide a scaffold for supporting the encapsulated cells.

In an embodiment, the modified polymer is an alginate. Alginate is a polysaccharide made up of β-D-mannuronic acid (M) and α-L-guluronic acid (G). In some embodiments, the alginate is a high guluronic acid (G) alginate, and comprises greater than about 50%, 55%, 60%, 65%, 70%, 75%, 80%, 85%, 90%, or more guluronic acid (G). In some embodiments, the ratio of G:M is at least 1.3, 1.5 or greater than 1.5. In some embodiments, the alginate is a high mannuronic acid (M) alginate, and comprises greater than about 50%, 55%, 60%, 65%, 70%, 75%, 80%, 85%, 90%, or more mannuronic acid (M). In some embodiments, the ratio of M:G is about 1. In some embodiments, the ratio of M:G is less than 1. In an embodiment, the polymer composition comprises a modified alginate and an unmodified alginate.

Polymers may be modified with a small molecule compound using any of a variety of methods known in the art, see, e.g., *Bioconjugate Techniques* ($3^{rd}$ ed, Greg T. Hermanson, Waltham, MA: Elsevier, Inc, 2013. For example, when the polymer to be modified is an alginate, and the small molecule compound comprises a terminal amine, the small molecule may be covalently bound to the carboxylate group of an alginate monomer using an approach similar to that described in Example 1 herein.

In some embodiments, the polymer composition further comprises a polymer modified with a polypeptide, e.g., a cell-binding peptide (CBP). Exemplary CBPs include sequences such as RGD, RGDSP, GRGD, GRGDSP, DGEA, PHSRN, YIGSR, or a CAM ligand protein. In an embodiment, a modified polymer comprises a mixture of 2, 3 or more CBPs (e.g., RGD+DGEA, RGD+PHSRN, RGD+DGEA+PHSRN).

The modified polymers described herein may be used to prepare a semi-permeable device encapsulating cells. In an embodiment, the semi-permeable devices may comprise a single type of modified polymer, or a plurality of types of modified polymers. These semi-permeable devices comprise at least one cell-containing compartment that comprises a plurality of cells (e.g., live cells). In an embodiment, the device contains two, three, four or more cell-containing compartments. The cells may be a variety of different cell types (e.g., human cells), including epithelial cells, endothelial cells, fibroblast cells, mesenchymal stem cells, keratinocyte cells and islet cells. Exemplary cell types include the cell types recited in WO 2017/075631, which is incorporated herein by reference in its entirety. In an embodiment, the cells are engineered cells, e.g., engineered to express a therapeutic agent (e.g., a protein, e.g., an antibody, enzyme, blood clotting factor, hormone, or growth factor).

In an embodiment, cells contained in a device of the disclosure comprise RPE cells or MSC cells (e.g., engineered RPE cells or engineered MSC cells). In some embodiments, the semi-permeable device does not comprise an islet cell. In an embodiment, the cells contained in a device of the disclosure have one or more of the following characteristics: (i) are not capable of producing insulin (e.g., insulin A-chain, insulin B-chain, or proinsulin) in an amount effective to treat diabetes or another disease or condition that may be treated with insulin; (ii) not capable of producing insulin in a glucose-responsive manner; or (iii) not derived from an induced pluripotent stem cell that was engineered or differentiated into insulin-producing pancreatic beta cells.

In an embodiment, the plurality of cells is in the form of a cell suspension prior to being encapsulated within a semi-permeable device described herein, e.g., a hydrogel capsule. The cells in the suspension may take the form of single cells (e.g., from a monolayer cell culture), or provided in another form, e.g., disposed on a microcarrier (e.g., a bead or matrix) or as a three-dimensional aggregate of cells (e.g., a cell cluster or spheroid). The cell suspension can comprise multiple cell clusters (e.g., as spheroids) or microcarriers.

In some embodiments, the cells in the plurality are engineered to produce a therapeutic agent. In an embodiment, the therapeutic agent is for the prevention or treatment of a disease, disorder, or condition, e.g., those described in WO 2017/075631. The therapeutic agent may be any biological substance, such as a nucleic acid (e.g., a nucleotide, DNA, or RNA), a polypeptide, a lipid, a sugar (e.g., a monosaccharide, disaccharide, oligosaccharide, or polysaccharide), or a small molecule. Exemplary therapeutic agents include the agents listed in WO 2017/075631.

In some embodiments, the therapeutic agent is a protein, such as a hormone, enzyme, cytokine (e.g., a pro-inflammatory cytokine or an anti-inflammatory cytokine), growth factor, clotting factor, or lipoprotein. A peptide or polypeptide (e.g., a protein, e.g., a hormone, growth factor, clotting factor or coagulation factor, antibody molecule, enzyme, cytokine, cytokine receptor, or a chimeric protein including cytokines or a cytokine receptor) produced by an engineered cell can have a naturally occurring amino acid sequence, or may contain a variant of the naturally occurring sequence. The variant can be a naturally occurring or non-naturally occurring amino acid substitution, mutation, deletion or addition relative to the reference sequence, e.g., a naturally occurring sequence. The naturally occurring amino acid sequence may be a polymorphic variant. The naturally occurring amino acid sequence can be a human or a non-human amino acid sequence. In some embodiments, the naturally occurring amino acid sequence or naturally occurring variant thereof is a human sequence. In addition, a protein for use with the present disclosure may be modified in some way, e.g., via chemical or enzymatic modification (e.g., glycosylation, phosphorylation). In some embodiments, the protein has an average molecular weight of 5 kD, 10 kD, 25 kD, 50 kD, 100 kD, 150 kD, 200 kD, 250 kD, 500 kD, or more.

In some embodiments, the protein is a clotting factor or a coagulation factor, e.g., a blood clotting factor or a blood coagulation factor. In some embodiments, the protein is a protein involved in coagulation, i.e., the process by which blood is converted from a liquid to solid or gel. Exemplary clotting factors and coagulation factors include Factor I (e.g., fibrinogen), Factor II (e.g., prothrombin), Factor III (e.g., tissue factor), Factor V (e.g., proaccelerin, labile factor), Factor VI, Factor VII (e.g., stable factor, proconvertin), Factor VIII (e.g., antihemophilic factor A), Factor VIIIC, Factor IX (e.g., antihemophilic factor B), Factor X (e.g., Stuart-Prower factor), Factor XI (e.g., plasma thromboplastin antecedent), Factor XII (e.g., Hagerman factor), Factor XIII (e.g., fibrin-stabilizing factor), von Willebrand factor (vWF), prekallikrein, heparin cofactor II, high molecular weight kininogen (e.g., Fitzgerald factor), antithrombin III, and fibronectin. In some embodiments, the protein is an anti-clotting factor, such as Protein C.

In some embodiments, the protein is a replacement therapy or a replacement protein. In some embodiments, the replacement therapy or replacement protein is a clotting factor or a coagulation factor, e.g., Factor VIII (e.g., comprises a naturally occurring human Factor VIII amino acid sequence or a variant thereof) or Factor IX (e.g., comprises a naturally occurring human Factor IX amino acid sequence or a variant thereof).

In some embodiments, the encapsulated cells described herein are engineered to express a human Factor VIII protein, e.g., a recombinant Factor VIII. In some embodiments, the recombinant Factor VIII is a B-domain-deleted recombinant Factor VIII (FVIII-BDD). In some embodiments, the cells are engineered to express a Factor IX, e.g., a human Factor IX (FIX) protein.

In some embodiments, the encapsulated cells are derived from a human RPE cell line and comprise an exogenous nucleic acid sequence which comprises a promoter sequence operably linked to a coding sequence for a polypeptide. In an embodiment, the coding sequence is a codon-optimized FVIII-BDD coding sequence or a codon-optimized FIX-padua coding sequence.

In an embodiment, the concentration of the small molecule compound (e.g., a compound of Formula (I)) in the modified polymer (e.g., afibrotic alginate) is defined as the % w/w, e.g., % of weight of small molecule/weight of modified polymer in solution (e.g., saline) as determined by an assay described herein. In certain embodiments, the concentration of a small molecule compound (e.g., a compound of Formula (I), e.g., Compound 101) is between about 1.0% w/w and about 3.0% w/w, between about 1.3% w/w and about 2.5 w/w or between about 1.5% w/w and 2.2% w/w.

In some embodiments, the concentration of a small molecule compound (e.g., an afibrotic compound, e.g., a compound of Formula (I)) present in the modified polymer is correlated with a specific parameter, e.g., retention time on a chromatogram or area under a curve on a chromatogram. In an embodiment, the small molecule compound is conjugated to the modified polymer or may be freely present in a sample, e.g., after hydrolysis. In an embodiment, the concentration of the small molecule compound (e.g., conjugated to a polymer, e.g., alginate) is between 0.1% and 10%, (w/w). For example, the concentration of the small molecule compound (e.g., conjugated to a polymer, e.g., alginate) is between 1% and 10%, 2% and 8%, 3% and 6%, 2% and 4%, 4% and 6%, or 6% and 8% (w/w). In an embodiment, the concentration of the small molecule compound (e.g., conjugated to a polymer, e.g., alginate) is between 4% and 6% (w/w). In an embodiment, the concentration of the small molecule compound (e.g., conjugated to a polymer, e.g., alginate) is between 2% and 4% (w/w).

In some embodiments, the semi-permeable device is not any capsule, device, implant or other object disclosed in any of WO2012/112982, WO2012/167223, WO2014/153126, WO2016/019391, WO2016/187225, US2012-0213708, US 2016-0030359, and US 2016-0030360.

Methods of Evaluating Modified Polymers

The present disclosure features methods for evaluating a polymer modified with a small molecule compound (e.g., afibrotic compound) within a polymer composition. Evaluating may include determining the small molecule compound (e.g., afibrotic compound) concentration of the modified polymer, identifying the small molecule compound in the modified polymer, or querying a polymer composition for certain impurities. The methods described herein include subjecting a sample of a modified polymer to reaction conditions capable of releasing the small molecule compound from the modified polymer. Once the small molecule compound (e.g., afibrotic compound) is liberated from the modified polymer, the concentration of the small molecule compound (e.g., afibrotic compound) in bound to the modified polymer may be determined, e.g., through chromatographic analysis.

Any reaction condition may be used in order to release the small molecule compound (e.g., afibrotic compound) from the modified polymer. For example, the polymer composition may be subjected to an acidic solution, a basic solution, an enzymatic solution, heat, light, microwave irradiation, hydrogenation, or a combination thereof. In an embodiment, the polymer composition is subjected to an acidic solution, such as solution comprising HCl, HBr, HF, $H_2SO_4$, $HNO_3$, $HClO_4$, $CF_3COOH$, $CH_3COOH$, or $CF_3SO_3H$, in order to release the small molecule compound (e.g., afibrotic compound) from the modified polymer. In an embodiment, an acidic solution has a pH less than 7, e.g., less 6.5, 6, 5.5, 5, 4.5, 4, 3.5, 3, 2.5, 2, 1.5, 1, or lower. The polymer composition may be subjected to heat, e.g., at a temperature greater than about 25° C., 40° C., 60° C., 80° C., 100° C., 120° C., or higher. In an embodiment, in order to release the small molecule compound (e.g., afibrotic compound) from the modified polymer, the polymer composition may be subjected to an acidic solution and heat, e.g., simultaneously. In an embodiment, the polymer composition is stirred while applying heat, e.g., using a stir plate.

In an embodiment, the polymer composition is subjected to microwave irradiation, e.g., for at least 1 seconds (s), 2 s, 5 s, 10 s, 15 s, 20 s, 25 s, 30 s, 35 s, 40 s, 45 s, 50 s, or 55 s, 1 minute (min), 2.5 min, 5 min, 10 min, 15 min, 20 min, 25 min, 30 min, 35 min, 40 min, 45 min, 50 min, 55 min, or 1 hour (hr). In an embodiment, the polymer composition is subject to microwave irradiation for between 1 min and 1 hr, e.g., between 1 min and 45 mins, 1 min and 30 mins, 1 min and 15 mins, 5 mins and 1 hr, 5 mins and 45 mins, 5 mins and 30 mins, 5 mins and 15 mins, 10 mins and 1 hr, 10 mins and 45 mins, 10 mins and 30 mins, 15 mins and 45 mins, and 15 mins and 30 mins. In an embodiment, the polymer composition is subjected to microwave irradiation for between 5 mins and 45 mins. In an embodiment, the polymer composition is stirred while applying microwave irradiation, e.g., at 100 revolutions per minute (rpm), 200 rpm, 300 rpm, 400 rpm, 500 rpm, 600 rpm, 700 rpm, 800 rpm or faster, e.g., in a microwave reactor (e.g., Anton-Paar Monowave microwave reactor). In an embodiment, the polymer composition is subjected to an acidic solution and microwave irradiation, e.g. simultaneously.

The methods described herein further comprise acquiring a value for the concentration of the small molecule compound (e.g., afibrotic compound) bound to a modified polymer within a polymer composition. To this end, in an embodiment, the composition of hydrolyzed polymer composition may be subjected to a separation step. Any known separation step may be used to separate the unconjugated small molecule compound (i.e., "free" small molecule compound) from the polymer, such as filtration, electrophoresis, or chromatography. Exemplary chromatographic methods include size-exclusion chromatography, ion-exchange chromatography, gel filtration chromatography, reversed-phase chromatography, hydrophobic interaction chromatography, or thin layer chromatography. In an embodiment, filtration is used to separate the unconjugated small molecule compound from the polymer in the polymer composition. After filtration, in an embodiment, the concentration of the free small molecule compound is subjected to reversed-phase chromatography to determine the concentration of the small molecule compound bound to the modified polymer.

In order to determine the concentration of small molecule compound in the polymer composition, the methods described herein may further comprise comparing the concentration of the small molecule compound in a sample with a known standard. Exemplary procedures are described herein, for example, in Examples 2-5 below.

The methods detailed herein may also be used to evaluate the impurity profile of a polymer composition. In an embodiment, the method further comprises acquiring the concentration of free small molecule compound (i.e., unconjugated small molecule compound) in the polymer composition, e.g., which was not previously bound to the modified polymer.

In the present disclosure features methods for evaluating a modified polymer comprising a small molecule compound within a polymer composition that do not entail subjecting the polymer composition to degradative conditions, e.g., hydrolytic conditions. For example, evaluating may comprise performing a non-degradative analysis method such as refractometry or spectroscopy on a sample of the polymer composition. In an embodiment, non-degradative methods of evaluating may include determining the overall concentration of the modified polymer in the sample, determining the concentration of the small molecule compound bound to the modified polymer in the sample, identifying a physical parameter (e.g., chemical formula, molecular weight, or atomic composition) of the small molecule compound bound to the modified polymer in the sample, or querying the polymer composition for certain impurities. In an embodiment, evaluating the polymer composition (e.g., in a non-degradative manner) comprises acquiring a value of the refractive index of the polymer composition, e.g., in a solid or liquid sample.

In order to use a refractive index to evaluate a polymer composition, e.g., described herein, the polymer composition may be dissolved in an aqueous medium, e.g., saline or other buffer (e.g., HEPES, sodium phosphate, Tris, or PBS). The refractive index of the polymer composition may be compared to a control sample, for example, comprising only the aqueous medium and not the polymer composition. In an embodiment, all samples are analyzed at the same wavelength of light and temperature.

In an embodiment, a specific refractive index increment value for each sample is determined (i.e., a "dn/dc value"). The specific refractive index increment is related to the amount by which the refractive index of a polymer composition changes with respect to another parameter, e.g., the amount of a small molecule compound in the composition (e.g., conjugated small molecule compound or unconjugated small molecule compound). In an embodiment, specific refractive index increment is provided as any dimension, e.g., g/mol or (1/% w/w). For example, for a polymer composition comprising a small molecule compound-modified alginate (e.g., a compound of Formula (I), e.g., Compound 101), a specific refractive index increment may be determined for each of the small molecule compound and a representative component of the alginate, such as a guluronic acid moiety. Exemplary methods are provided herein in Example 5.

The refractive index (nD) of a polymer composition may be between 1.3300 and 1.3400, e.g., at a specific temperature or temperature range (e.g., between about 2-8° C., or about 22-28° C.). For example, the refractive index of a polymer composition described herein may be between 1.3310 and 1.3400, e.g., 1.3320 and 1.3400, 1.3330 and 1.3400, 1.3340 and 1.3400, 1.3360 and 1.3400, 1.3370 and 1.3400, and 1.3380 and 1.3400. In an embodiment, the refractive index of a polymer composition is between 1.3350 and 1.3400.

ENUMERATED EMBODIMENTS

1. A method of evaluating a polymer composition comprising a polymer modified with a compound of Formula (I-b):

(I-b)

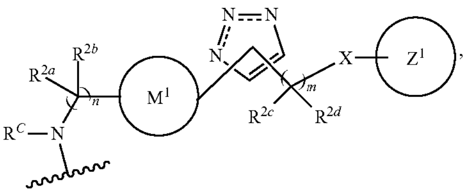

or a pharmaceutically acceptable salt thereof, wherein:

Ring is aryl or heteroaryl, wherein each aryl and heteroaryl is optionally substituted with one or more $R^3$;

Ring $Z^1$ is cycloalkyl, heterocyclyl, aryl, or heteroaryl, wherein each cycloalkyl, heterocyclyl, aryl, or heteroaryl is optionally substituted with 1-5 $R^5$;

each of $R^{2a}$ and $R^{2b}$, $R^{2c}$, and $R^{2d}$ is independently hydrogen, alkyl, or heteroalkyl, or each of $R^{2a}$, $R^{2b}$, $R^{2c}$, and $R^{2d}$ is taken together to form an oxo group;

X is absent, O, or S;

each $R^3$ and $R^5$ is independently alkyl, heteroalkyl, halogen, oxo, —C(O)$OR^{A1}$, or —C(O)$R^{B1}$, wherein each alkyl and heteralkyl is optionally substituted with one or more halogen, oxo, cyano, cycloalkyl, or heterocyclyl; or two $R^5$ are taken together to form a 5-6 membered ring fused to Ring $Z^1$;

$R^C$ is hydrogen or alkyl;

each $R^{A1}$ and $R^{B1}$ is independently hydrogen, alkyl, or heteroalkyl;

m and n are each independently 1, 2, 3, 4, 5, or 6; and

"∿∿∿ " refers to a connection to an attachment group or the polymer;

the method comprising:

(a) subjecting the polymer composition to reaction conditions that allow for release of the compound of Formula (I-b) from the modified polymer; and (b) acquiring a value of the concentration of the compound of Formula (I-b) bound to the modified polymer, thereby evaluating the polymer composition or semi-permeable device.

2. A method of evaluating a polymer composition comprising a polymer modified with a compound of Formula (III-a):

(III-a)

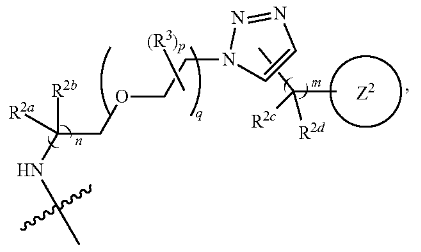

or a pharmaceutically acceptable salt thereof, wherein:

Ring $Z^2$ is cycloalkyl, heterocyclyl, aryl, or heteroaryl, each of which is optionally substituted with 1-5 $R^5$;

each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$, and $R^{2d}$ are taken together to form an oxo group;

each of $R^3$ and $R^5$ is independently alkyl, heteroalkyl, halogen, oxo, —$OR^{A1}$, —C(O)$OR^{A1}$, or —C(O)$R^{B1}$;

each $R^{A1}$ and $R^{B1}$ is independently hydrogen, alkyl, or heteroalkyl;

m and n are each independently 1, 2, 3, 4, 5, or 6;

and p are each independently 0, 1, 2, 3, 4, or 5;

q is an integer from 0 to 25; and

"∿∿∿ " refers to a connection to an attachment group or the polymer;

the method comprising:

(a) subjecting the polymer composition to reaction conditions that allow for release of the compound of Formula (III-a) from the modified polymer; and (b) acquiring a value of the concentration of the compound of Formula (III-a), thereby evaluating the polymer composition or semi-permeable device.

3. The method of any one of embodiments 1-2, wherein the polymer in the modified polymer is a polysaccharide.

4. The method of embodiment 3, wherein the polysaccharide is an alginate.

5. The method of embodiment 4, wherein the alginate has an average molecular weight of 75 kD to 150 kD.

6. The method of any one of embodiments 4-5, wherein the alginate has a guluronate to mannuronate (G:M) ratio of greater than or equal to 1.5.

7. The method of any one of embodiments 1-6, wherein the compound of Formula (I-b) or Formula (III-a) is covalently bound to the polymer (e.g., alginate) in the modified polymer.

8. The method of any one of embodiments 1-6, wherein the compound of Formula (I-b) or Formula (III-a) is non-covalently bound to the polymer (e.g., alginate) in the modified polymer.

9. The method of any one of embodiments 1-6, wherein the compound of Formula (I-b) or Formula (III-a) is covalently bound to the modified polymer (e.g., modified alginate) through an attachment group (e.g., —C(O)($C_1$-$C_6$-alkylene)-, wherein alkylene is substituted with $R^1$, and $R^1$ is as described herein).

10. The method of any one of embodiments 1-9, wherein the polymer composition comprises a single type of modified polymer (e.g., modified alginate).

11. The method of any one of embodiments 1-9, wherein the polymer composition comprises a plurality of modified polymers (e.g., at least two modified polymers, at least three modified polymers).

12. The method of any one of embodiments 1-11, wherein the compound of Formula (I-b) or Formula (III-a) is a compound listed in Table 1.

13. The method of any one of embodiments 1-12, wherein the compound of Formula (I-b) or Formula (III-a) is selected from Compound 100, Compound 101, Compound 110, Compound 113, and Compound 114 listed in Table 1.

14. The method of any one of embodiments 1-13, wherein the compound of Formula (I-b) or Formula (III-a) is Compound 100 listed in Table 1.

15. The method of any one of embodiments 1-13, wherein the compound of Formula (I-b) or Formula (III-a) is Compound 101 listed in Table 1.

16. The method of any one of embodiments 1-13, wherein the compound of Formula (I-b) or Formula (III-a) is Compound 110 listed in Table 1.

17. The method of any one of embodiments 1-13, wherein the compound of Formula (I-b) or Formula (III-a) is Compound 113 listed in Table 1.

18. The method of any one of embodiments 1-13, wherein the compound of Formula (I-b) or Formula (III-a) is Compound 114 listed in Table 1.

19. The method of any one of embodiments 1-18, wherein the reaction conditions in step (a) comprise contacting the polymer composition with an acidic solution (e.g., an HCl solution, e.g., a 1N-8N HCl solution).

20. The method of any one of embodiments 1-19, wherein the reaction conditions in step (a) comprise heating the polymer composition (e.g., at a temperature greater than about 25° C., 40° C., 60° C., 80° C., 100° C., 120° C., or higher).

21. The method of any one of embodiments 1-20, wherein the reaction conditions in step (a) comprise exposing the polymer composition to microwave irradiation.

22. The method of any one of embodiments 1-21, further comprising a separation step.

23. The method of embodiment 22, wherein the separation step occurs between step (a) and step (b).

24. The method of any one of embodiments 22-23, wherein the separation step comprises chromatography (e.g., size-exclusion chromatography, ion-exchange chromatography, gel filtration chromatography, reversed-phase chromatography, or hydrophobic interaction chromatography).

25. The method of any one of embodiments 1-24, wherein acquiring a value for the concentration in step (b) comprises determining the area of a chromatogram peak for the compound of Formula (I-b) or Formula (III-a).

26. The method of embodiment 25, wherein acquiring a value of the concentration in step (b) further comprises comparing the area of a chromatogram peak with a standard, e.g., a compound of Formula (I-b) or Formula (III-a).

27. The method of any one of embodiments 1-26, further comprising acquiring a value of the concentration of an unconjugated compound of Formula (I-b) (i.e., "free" compound of Formula (I-b)) or an unconjugated compound of Formula (III-a) (i.e., "free" compound of Formula (III-a)) in the polymer composition.

28. The method of embodiment 27, wherein acquiring a value of the concentration of the unconjugated compound of Formula (I-b) (i.e., "free" compound of Formula (I-b)) or the unconjugated compound of Formula (III-a) (i.e., "free" compound of Formula (III-a)) in the polymer composition comprises:

(a') separating the polymer composition into a polymer bound fraction and a non-polymer bound fraction.

29. The method of any one of embodiments 27-28, further comprising:

(b') retaining the non-polymer bound fraction.

30. The method of any one of embodiments 27-29, further comprising:

(c') acquiring a value of the concentration of the unconjugated compound of Formula (I-b) (i.e., "free" compound of Formula (I-b)) or the unconjugated compound of Formula (III-a) (i.e., "free" compound of Formula (III-a)) in the non-polymer bound fraction.

31. The method of any one of embodiments 27-30, wherein the separating of step (a') comprises filtration, e.g., with a molecular weight cutoff filter.

32. The method of any one of embodiments 27-31, wherein step (c') comprises a separation step.

33. The method of embodiment 32, wherein the separation step comprises chromatography (e.g., size-exclusion chromatography, ion-exchange chromatography, gel filtration chromatography, reversed-phase chromatography, or hydrophobic interaction chromatography).

34. The method of any one of embodiments 27-33, wherein acquiring a value of the concentration in step (c') further comprises determining the area of a chromatogram peak of a sample of the unconjugated compound of Formula (I-b) (i.e., "free" compound of Formula (I-b)) or the unconjugated compound of Formula (III-a) (i.e., "free" compound of Formula (III-a)) in the non-polymer bound fraction.

35. The method of embodiment 34, wherein acquiring a value of the concentration in step (c') further comprises comparing the area of a chromatogram peak with a standard, e.g., a compound of Formula (I-b) or Formula (III-a).

36. The method of any one of embodiments 1-35, wherein evaluating a polymer composition comprises determining the concentration of a compound of Formula (I-b) or Formula (III-a) bound to a modified polymer in the polymer composition.

37. The method of embodiment 36, wherein determining the concentration of a compound of Formula (I-b) or Formula (III-a) bound to a modified polymer in the polymer composition comprises:

(a") acquiring a value for the total concentration of the compound of Formula (I-b) or Formula (III-a) in the polymer composition;

(b") acquiring a value for the concentration of the unconjugated compound of Formula (I-b) (i.e., "free" compound of Formula (I-b)) or the unconjugated compound of Formula (III-a) (i.e., "free" compound of Formula (III-a)) in the polymer composition; and/or (c") subtracting the value of the concentration of free compound of Formula (I-b) or free compound of Formula (III-a) (e.g., as determined in step (b")) from the value of the total concentration of the compound of Formula (I-b) or Formula (III-a) in the polymer composition, thereby determining the concentration of the compound of Formula (I-b) or Formula (III-a) conjugated (e.g., covalently bound) to a modified polymer in the polymer composition.

38. The method of embodiment 37, comprising (a").

39. The method of any one of embodiments 37-38, comprising (b").

40. The method of any one of embodiments 37-39, comprising (c").

41. A method of determining the concentration of a polymer composition comprising an alginate covalently modified with a compound of Formula (I-b):

(I-b)

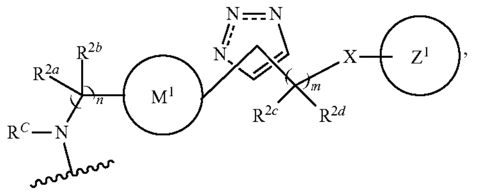

or a pharmaceutically acceptable salt thereof, wherein:

Ring $M^1$ is aryl or heteroaryl, wherein each aryl and heteroaryl is optionally substituted with one or more $R^3$;

Ring $Z^1$ is cycloalkyl, heterocyclyl, aryl, or heteroaryl, wherein each cycloalkyl, heterocyclyl, aryl, or heteroaryl is optionally substituted with 1-5 $R^5$;

each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group;

X is absent, O, or S;

each $R^3$ and $R^5$ is independently alkyl, heteroalkyl, halogen, oxo, —C(O)O$R^{A1}$, or —C(O)$R^{B1}$, wherein each alkyl and heteralkyl is optionally substituted with one or more halogen, oxo, cyano, cycloalkyl, or heterocyclyl; or two $R^5$ are taken together to form a 5-6 membered ring fused to Ring $Z^1$;

$R^C$ is hydrogen or alkyl;

each $R^{A1}$ and $R^{B1}$ is independently hydrogen, alkyl, or heteroalkyl;

m and n are each independently 1, 2, 3, 4, 5, or 6; and

"∿∿∿ " refers to a connection to an attachment group or the polymer or a compound of Formula (III-a):

(III-a)

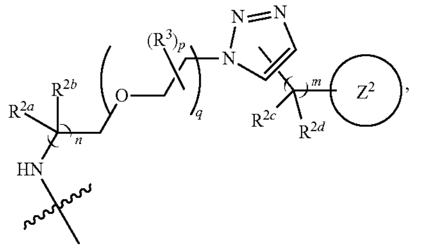

or a pharmaceutically acceptable salt thereof, wherein:

Ring $Z^2$ is cycloalkyl, heterocyclyl, aryl, or heteroaryl, each of which is optionally substituted with 1-5 $R^5$;

each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group;

each of $R^3$ and $R^5$ is independently alkyl, heteroalkyl, halogen, oxo, —$OR^{A1}$, —$C(O)OR^{A1}$, or —$C(O)R^{B1}$;

each $R^{A1}$ and $R^{B1}$ is independently hydrogen, alkyl, or heteroalkyl;

m and n are each independently 1, 2, 3, 4, 5, or 6;

and p are each independently 0, 1, 2, 3, 4, or 5;

q is an integer from 0 to 25; and

“∿∿∿ ” refers to a connection to an attachment group or the polymer the method comprising:

(a) acquiring a value for the total concentration of the compound of Formula (I-b) or Formula (III-a) in the polymer composition.

42. The method of embodiment 41, further comprising:

(b) acquiring a value for the concentration of the unconjugated compound of Formula (I-b) (i.e., “free” compound of Formula (I-b)) or the unconjugated compound of Formula (III-a) (i.e., “free” compound of Formula (III-a)) in the polymer composition.

43. The method of any one of embodiments 41-42, further comprising:

(c) subtracting the value of the concentration of free compound of Formula (I-b) or free compound of Formula (III-a) (e.g., as determined in step (b)) from the value of the total concentration of the compound of Formula (I-b) or Formula (III-a) in the polymer composition.

44. The method of any one of embodiments 41-43, wherein step (a) is performed prior to step (b).

45. The method of any one of embodiments 41-43, wherein step (b) is performed prior to step (a).

46. The method of any one of embodiments 41-45, wherein step (a) comprises:

(a) subjecting the polymer composition to reaction conditions that allow for release of the compound of Formula (I-b) or Formula (III-a) from the modified polymer; and (b) acquiring a value of the concentration of the compound of Formula (I-b) or of the compound of Formula (III-a).

47. The method of any one of embodiments 41-46, wherein the compound is a compound of Formula (I-b).

48. The method of embodiment 47, wherein the compound is Compound 100, Compound 110, Compound 113, or Compound 114, or a pharmaceutically acceptable salt thereof.

49. The method of any one of embodiments 41-46, wherein the compound is a compound of Formula (III-a).

50. The method of embodiment 49, wherein the compound is Compound 101, or a pharmaceutically acceptable salt thereof.

51. The method of any one of embodiments 1-50, wherein the concentration of the compound of Formula (I-b) or compound of Formula (III-a) bound to polymer in a modified polymer (e.g., modified alginate) is between about 0.5% and 10% (w/w) modified polymer (e.g., modified alginate), e.g., between about 0.5% and 5%, 1% and 5%, 1% and 4%, or 1 and 3% (w/w) modified polymer (e.g., modified alginate).

52. The method of any one of embodiments 1-51, wherein the concentration of free compound of Formula (I-b) or free compound of Formula (III-a) in the polymer composition is less than about 1% (w/w) modified polymer (e.g., modified alginate), e.g., less than about 0.9%, 0.8%, 0.7%, 0.6%, or 0.5% (w/w) modified polymer (e.g., modified alginate).

53. A method of evaluating a polymer composition comprising a polymer modified with a compound of Formula (I-b):

(I-b)

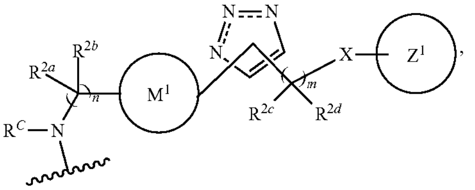

or a pharmaceutically acceptable salt thereof, wherein:

Ring $M^1$ is aryl or heteroaryl, wherein each aryl and heteroaryl is optionally substituted with one or more $R^3$;

Ring $Z^1$ is cycloalkyl, heterocyclyl, aryl, or heteroaryl, wherein each cycloalkyl, heterocyclyl, aryl, or heteroaryl is optionally substituted with 1-5 $R^5$;

each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group;

X is absent, O, or S;

each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteralkyl is optionally substituted with one or more halogen, oxo, cyano, cycloalkyl, or heterocyclyl; or two $R^5$ are taken together to form a 5-6 membered ring fused to Ring $Z^1$;

$R^C$ is hydrogen or alkyl;

each $R^{A1}$ and $R^{B1}$ is independently hydrogen, alkyl, or heteroalkyl;

m and n are each independently 1, 2, 3, 4, 5, or 6; and

“∿∿∿ ” refers to a connection to an attachment group or the polymer or a compound of Formula (III-a):

(III-a)

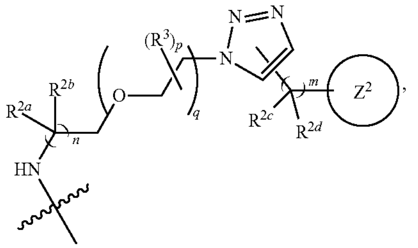

or a pharmaceutically acceptable salt thereof, wherein:

Ring $Z^2$ is cycloalkyl, heterocyclyl, aryl, or heteroaryl, each of which is optionally substituted with 1-5 $R^5$;

each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group;

each of $R^3$ and $R^5$ is independently alkyl, heteroalkyl, halogen, oxo, —$OR^{A1}$, —$C(O)OR^{A1}$, or —$C(O)R^{B1}$;

each $R^{A1}$ and $R^{B1}$ is independently hydrogen, alkyl, or heteroalkyl;

m and n are each independently 1, 2, 3, 4, 5, or 6;

and p are each independently 0, 1, 2, 3, 4, or 5;

q is an integer from 0 to 25; and

"∿∿∿ " refers to a connection to an attachment group or the polymer the method comprising:

(a) acquiring a value for the refractive index of the polymer composition.

54. The method of embodiment 53, further comprising:

(b) acquiring a value for the total unconjugated compound of Formula (I-b) (i.e., "free" compound of Formula (I-b)) or the total unconjugated compound of Formula (III-a) (i.e., "free" compound of Formula (III-a)) in the polymer composition.

55. The method of any one of embodiments 53-54, further comprising:

(c) acquiring a value for the concentration of the polymer modified with a compound of Formula (I-b) or Formula (III-a).

56. The method of embodiment 55, wherein the acquiring comprises using the values obtained in each of steps (a) and (b).

57. The method of any one of embodiments 53-56, wherein the polymer is an alginate.

58. The method of embodiment 57, wherein the alginate has an average molecular weight of 75 kD to 150 kD.

59. The method of any one of embodiments 57-58, wherein the alginate has a guluronate to mannuronate (G:M) ratio of greater than or equal to 1.5.

60. The method of any one of embodiments 53-59, wherein the compound of Formula (I-b) or Formula (III-a) is covalently bound to the polymer (e.g., alginate) in the modified polymer.

61. The method of any one of embodiments 53-59, wherein the compound of Formula (I-b) or Formula (III-a) is non-covalently bound to the polymer (e.g., alginate) in the modified polymer.

62. The method of any one of embodiments 53-59, wherein the compound of Formula (I-b) or Formula (III-a) is covalently bound to the modified polymer (e.g., modified alginate) through an attachment group (e.g., —$C(O)(C_1$-$C_6$-alkylene)-, wherein alkylene is substituted with and $R^1$ is as described herein).

63. The method of any one of embodiments 53-62, wherein the polymer composition comprises a single type of modified polymer (e.g., modified alginate).

64. The method of any one of embodiments 53-62, wherein the polymer composition comprises a plurality of modified polymers (e.g., at least two modified polymers, at least three modified polymers).

65. The method of any one of embodiments 53-64, wherein the compound of Formula (I-b) or Formula (III-a) is a compound listed in Table 1.

66. The method of any one of embodiments 53-65, wherein the compound of Formula (I-b) or Formula (III-a) is selected from Compound 100, Compound 101, Compound 110, Compound 113, and Compound 114 listed in Table 1.

67. The method of any one of embodiments 53-66, wherein the compound of Formula (I-b) or Formula (III-a) is Compound 100 listed in Table 1.

68. The method of any one of embodiments 53-66, wherein the compound of Formula (I-b) or Formula (III-a) is Compound 101 listed in Table 1.

69. The method of any one of embodiments 53-66, wherein the compound of Formula (I-b) or Formula (III-a) is Compound 110 listed in Table 1.

70. The method of any one of embodiments 53-66, wherein the compound of Formula (I-b) or Formula (III-a) is Compound 113 listed in Table 1.

71. The method of any one of embodiments 53-66, wherein the compound of Formula (I-b) or Formula (III-a) is Compound 114 listed in Table 1.

72. The method of any one of embodiments 53-71, wherein acquiring a value of the total compound of Formula (I-b) or Formula (III-a) conjugated (e.g., covalently bound) to a modified polymer composition of step (b) comprises:

(b') subjecting the polymer composition to reaction conditions that allow for:

(i) release of the compound of Formula (I-b) or Formula (III-a) from the modified polymer; and (b") acquiring a value of the concentration of the compound of Formula (I-b) or of the compound of Formula (III-a).

73. The method of any one of embodiments 53-72, further comprising acquiring a dn/dc value for a component of the polymer composition (e.g., a component of the modified polymer).

74. The method of embodiment 73, further comprising using the dn/dc value in step (c) of the method, e.g., to acquire a value for the concentration of the polymer modified with the compound of Formula (I-b) or Formula (III-a).

75. A method of determining the concentration of a compound of Formula (I-b) or Formula (III-a) bound to alginate in a polymer composition, the method comprising:

(a) acquiring a value for the refractive index of the polymer composition;

(b) acquiring a value of the total compound of Formula (I-b) or Formula (III-a) conjugated (e.g., covalently bound) to a modified polymer in the polymer composition; and/or (c) using the values obtained in each of steps (a) and (b), acquiring a value for the concentration of the compound of Formula (I-b) or Formula (III-a) conjugated to a modified polymer;

thereby determining the concentration of a compound of Formula (I-b) or Formula (III-a) bound to a polymer in a polymer composition.

76. The method of embodiment 75, comprising (a).

77. The method of any one of embodiments 75-76, comprising (b).

78. The method of any one of embodiments 75-77, comprising (c).

79. The method of any one of embodiments 75-78, wherein the compound is a compound of Formula (I-b).

80. The method of embodiment 79, wherein the compound is Compound 100, Compound 110, Compound 113, or Compound 114, or a pharmaceutically acceptable salt thereof.

81. The method of any one of embodiments 75-78, wherein the compound is a compound of Formula (III-a).

82. The method of embodiment 81, wherein the compound is Compound 101, or a pharmaceutically acceptable salt thereof.

83. A polymer composition comprising a polymer modified with a compound of Formula (I-b) or a compound of Formula (III-a), wherein the concentration of the compound of Formula (I-b) or compound of Formula (III-a) is between 0.5% and 5% (w/w) modified alginate, e.g., as determined by a method of any one of embodiments 1-82.

84. A polymer composition comprising an alginate modified with a compound of Formula (I-b) or a compound of Formula (III-a), wherein the concentration of the compound of Formula (I-b) or compound of Formula (III-a) is between 0.5% and 5% (w/w) modified alginate, e.g., as determined by a method of any one of embodiments 1-82.

85. A polymer composition comprising an alginate modified with a compound selected from Compound 100, Compound 101, Compound 110, Compound 112, Compound 113, and/or Compound 114 as shown in Table 1, wherein the concentration of the compound is between 0.5% and 5% (w/w) modified alginate, e.g., as determined by a method of any one of embodiments 1-82.

EXAMPLES

In order that the disclosure described herein may be more fully understood, the following examples are set forth. The examples described in this application are offered to illustrate the devices (e.g., capsules, particles, chemical modifications, compositions and methods provided herein and are not to be construed in any way as limiting their scope.

Example 1. Preparation of Exemplary Modified Polymers

A polymeric material may be chemically modified with a small molecule compound (e.g., an afibrotic compound) or pharmaceutically acceptable salt thereof prior to formation of a semi-permeable device (e.g., a hydrogel capsule) using methods known in the art.

For example, in the case of alginate, the alginate carboxylic acid is activated for coupling to one or more amine-functionalized compounds to achieve an alginate modified with an afibrotic compound, e.g., a compound of Formula (I). The alginate polymer is dissolved in water (30 mL/gram polymer) and treated with 2-chloro-4,6-dimethoxy-1,3,5-triazine (0.5 eq) and N-methylmorpholine (1 eq). To this mixture is added a solution of the compound of interest (e.g., Compound 101 shown in Table 4) in acetonitrile (0.3M). A compound of interest may be prepared using methods known in the art, for example, as described in WO2018/067615, which is incorporated herein by reference in its entirety.

The amounts of the compound and coupling reagent added depends on the desired concentration of the compound bound to the alginate. To prepare a CM-LMW-Alg-101-Medium polymer solution, the dissolved unmodified low molecular weight alginate (approximate MW<75 kDa, G:M ratio≥1.5) is treated with 2-chloro-4,6-dimethoxy-1,3,5-triazine (5.1 mmol/g alginate) and N-methylmorpholine (10.2 mmol/g alginate) and Compound 101 (5.4 mmol/g alginate). To prepare a CM-LMW-Alg-101-High polymer solution, the dissolved unmodified low-molecular weight alginate (approximate MW<75 kDa, G:M ratio≥1.5) is treated with 2-chloro-4,6-dimethoxy-1,3,5-triazine (5.1 mmol/g alginate) and N-methylmorpholine (10.2 mmol/g alginate) and Compound 101 (5.4 mmol/g alginate).

The reaction is warmed to 55° C. for 16 h, then cooled to room temperature and gently concentrated via rotary evaporation, then the residue is dissolved in water. The mixture is filtered through a bed of cyano-modified silica gel (Silicycle) and the filter cake is washed with water. The resulting solution is then extensively dialyzed (10,000 MWCO membrane) and the alginate solution is concentrated via lyophilization to provide the desired chemically modified alginate as a solid or is concentrated using any technique suitable to produce a chemically modified alginate solution with a viscosity of 25 cP to 35 cP.

In an embodiment, concentration of the small molecule compound bound to the alginate is determined using the protocols described in Examples 2-5 below. as described in Example 27 below.

Example 2. Determining Total Afibrotic Compound in a Afibrotic Compound-Modified Sample To determine the total amount of an afibrotic compound (including both free afibrotic compound and conjugated afibrotic compound) in a polymer composition, the polymer composition may be subjected to acid hydrolysis to cleave the conjugated afibrotic compound from the modified polymer. The concentration of the resulting unconjugated afibrotic compound can then be determined, e.g., using high-pressure liquid chromatography (HPLC). Here, the total afibrotic compound was quantified in a sample of modified alginate as described below.

Acid hydrolysis modified polymer. 50±5 mg of lyophilized solid alginate modified with an afibrotic compound, or a solution of alginate modified with an afibrotic compound in saline (1000±50 mg) was weighed into a reaction vial, ensuring the solid remained at the bottom of the vial. Then 2N HCl (10 mL) was added to the vial with a stir bar. The sealed vial was heated to 120° C. and stirred at 400 rpm for 120 minutes, then cooled to ambient temperature. The entire solution was then transferred to a 25 mL volumetric flask, and the empty reaction vial was rinsed thoroughly three times with 5 mL of LCMS grade water and transferred to the volumetric flask (using the same pipette to ensure complete transfer of the sample). The volumetric flask was then brought to volume with LCMS grade water, transferred to a 50 mL centrifuge tube and centrifuged at 3000 revolutions per minute (rpm) for 10 minutes. The supernatant was then analyzed by HPLC analysis and/or stored at 2-8° C. until use.

Alternatively, hydrolysis of the afibrotic compound-modified alginate (Compound 101-conjugated alginate) was carried out by microwave irradiation. Briefly, 1000±50 mg of afibrotic compound-conjugated alginate in saline solution was weighed into a microwave vial. 6N HCl (10 mL) solution was then added to the vial with a stir bar, and the vial was capped and placed into a microwave autosampler. Each sample was processed according to the following conditions:

| Parameter | Setting | Stir RPM |
|---|---|---|
| Ramp Time | AFAP | 400 |
| Hold Temp | 152° C. | 400 |
| Hold Time | 20 min | 400 |
| Cooling Temp | 55° C. | 400 |

Each vial was removed and the contents were transferred into a volumetric flask, to which 2 mL of LCMS grade water was added (2×). The flask was capped and inverted to mix, then the contents were transferred to a 50 mL centrifuge tube. The sample was centrifuged at 5000 rpm for approximately 10 minutes. 1 mL of the supernatant was then transferred to an LC vial and stored at 2-8° C. overnight. The next day, the sample was heated to 60° C. and completely dried by placing a needle delivering a nitrogen stream directly over the sample (ensuring the needle did not touch the sample). Once dried, 0.25 mL of the 0.1 μmol/mL internal standard mixture (see preparation below) was added to the LC vial, the solution was vortexed thoroughly, then transferred to a second LC vial with a 0.25 mL insert. The sample was stored at 2-8° C. until use.

HPLC conditions. HPLC was performed with an Agilent 1260 LC with DAD and SQ MS, using an)(Bridge C18, 2.5 μm, 4.6×50 mm (Waters 186006037) column, and equipped with an API-ES MS detector. The mobile aqueous phase used was 0.1% ammonia, and the mobile organic phase was 0.1% ammonia in acetonitrile, at a flow rate of 1.0 mL/min. The column was at 30° C. The UV detector was set to a wavelength of 220 nm.

Samples were injected at a volume of 10 μL, following a set sequence. First, two blank sample of water were injected in sequence, followed by five replicates of the 0.01 mg/mL free amine standard. Then, samples were run in sequence, and every 10 samples were bracketed with an injection of the standard free afibrotic compound solution. The HPLC sequence was ended with an injection of the 1.0 mg/mL afibrotic compound standard, followed by a column flush with 50/50 water-acetonitrile. An exemplary HPLC chromatogram obtained from an acid-hydrolyzed sample to determine total afibrotic compound concentration is shown in FIG. 1.

System suitability criteria. Data was checked against the suitability criteria as follows: no significant interference in UV and TIC (optional); no more than 2% relative standard deviation (RSD) of retention time in the first 5 injections; no more than 10% RSD of area in the first 5 injections; no more than 2% RSD of retention time in the first 5 injections and all bracketing injections; no more than 10% RSD of area in the first 5 injections and all bracketing injections; and optionally an afibrotic compound peak with m/z of 392.1±0.5.

Data analysis and calculations. The total afibrotic compound concentration in the sample (mg/mL) was calculated using the following formula: [conc. total afibrotic compound (mg/mL)]=[area (hydrolyzed sample)]/[area (1.0 mg/mL standard)]×[concentration (1.0 mg/mL standard)]

The concentration of total afibrotic compound in the modified alginate (%) was calculated using the following formula: concentration of total afibrotic compound in the modified alginate (%)=[concentration of total afibrotic compound in sample (mg/mL)]×25 mL/[weight of modified alginate (mg)×100]

Example 3. Determining Free Afibrotic Compound in Afibrotic Compound-Modified Alginate To determine the amount of unconjugated afibrotic compound (i.e., "free" afibrotic compound) in a sample of total modified polymer (e.g., afibrotic alginate), the free afibrotic compound can be separated from the modified polymer and quantified. Here, the free afibrotic compound was separated from a sample of modified alginate and quantified using the following procedures.

Sample Preparation. A lyophilized solid sample of afibrotic alginate (50±5 mg) was weighed into a scintillation vial, followed by the addition of 5.0 mL of saline. The mixture was then completely dissolved by shaking and vortexing the mixture for 10 minutes, and then transferred to a tube fitted with a molecular weight cut-off (MWCO) filter. The MWCO tube was then centrifuged at 5000 rpm for 60 minutes. After centrifugation, the supernatant above the MWCO filter containing afibrotic alginate was removed from the tube and discarded. The sample from the bottom of the MWCO tube containing free afibrotic compound was then transferred to a 5 mL volumetric flask, and brought to volume with water or saline and inverted to mix well. The solution was subsequently stored in a scintillation vial at 2-8° C.

Solutions of the afibrotic alginate in saline solution were also analyzed in the same way outlined above, by adding 1000±50 mg of the afibrotic alginate in saline to a MWCO tube with an additional 4 mL saline, and the tube was centrifuged for 90 minutes.

Preparation of free amine standard solutions. 50±5 mg of afibrotic compound (standard) was weighed into a scintillation vial, followed by approximately 10 mL of LCMS-grade water, and the solid was dissolved completely by shaking and vortexing. The solution was then transferred to a 50 mL volumetric flask, and the vial was further rinsed twice with LCMS grade water and transferred to the volumetric flask. The volumetric flask was then brought to volume and mixed well to provide a 1 mg/mL free afibrotic compound standard solution. A 0.01 mg/mL free afibrotic compound standard solution was also prepared by transferring 100 μL of the 1 mg/mL standard solution to a 10 mL volumetric flask, bringing the flask to volume with LCMS-grade water, and mixing well. Both standard solutions were stored at 2-8° C.

HPLC conditions. HPLC was performed as outlined in Example 2.

Figure 2B:
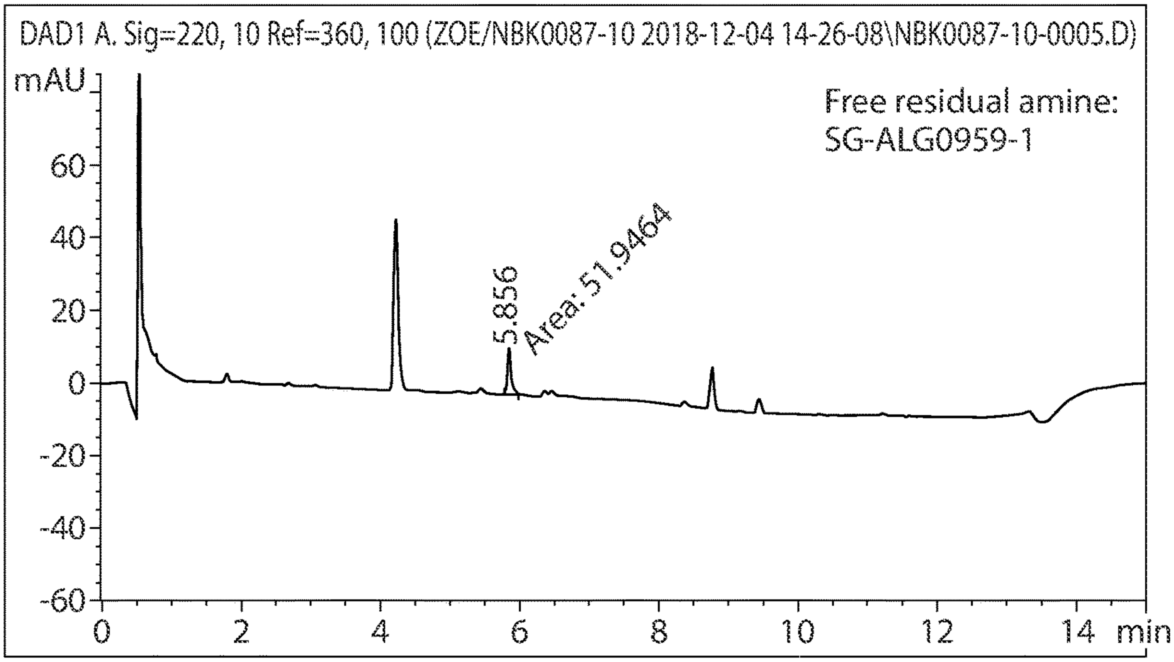

Samples were injected at a volume of 10 μL, following a set sequence. First, two blank sample of water were injected in sequence, followed by five replicates of the 0.01 mg/mL free afibrotic compound standard. Then, samples were run in sequence, and every 10 samples were bracketed with an injection of the standard free afibrotic compound solution. The HPLC sequence was ended with an injection of the 1.0 mg/mL free afibrotic compound standard, followed by a column flush with 50/50 water-acetonitrile. Exemplary HPLC chromatograms can be found in FIGS. 2A-2B, including the standard sample (FIG. 2A), and an exemplary sample containing free afibrotic compound (FIG. 2B).

System suitability criteria. Data was checked against the suitability criteria as follows: no significant interference in UV and TIC (optional); no more than 2% relative standard deviation (RSD) of retention time in the first 5 injections; no more than 10% RSD of area in the first 5 injections; no more than 2% RSD of retention time in the first 5 injections and all bracketing injections; no more than 10% RSD of area in the first 5 injections and all bracketing injections; and optionally an afibrotic compound peak with m/z of 392.1±0.5.

Data analysis and calculations. The free afibrotic compound peak was identified as having an m/z of 392.1±0.5, and having a retention time matching the peak found in the standard free afibrotic compound solution.

The concentration of the standard free afibrotic compound solution (mg/mL) was calculated using the following formula: standard free afibrotic compound concentration (mg/mL)=[weight of free afibrotic compound (mg)]/50 mL/dilution factor; where dilution factor is 1 for a 1.0 mg/mL free afibrotic compound standard; or 100 for the 0.01 mg/mL free amine standard.

The concentration of free afibrotic compound in the sample (mg/mL) was calculated with HPLC data, using the following formula: concentration of free afibrotic compound in sample (mg/mL)=area (free afibrotic compound sample)/[area (free afibrotic compound standard)]×[concentration of free afibrotic compound standard (mg/mL)].

The concentration of free afibrotic compound (%) in the modified alginate was then calculated using the following formula: concentration of free afibrotic compound in modified alginate (%)={[concentration free afibrotic compound in sample (mg/mL)]×5 mL}/[(mass of modified alginate)×100].

Example 4. Determining Conjugated Afibrotic Compound in an Afibrotic Compound-Modified Polymer When the amount of free afibrotic compound and total afibrotic compound (free afibrotic compound+conjugated afibrotic compound) in a sample of modified polymer is known, the amount of conjugated afibrotic compound in the modified polymer can be readily calculated. In cases where the amount of free afibrotic compound is less than 2%, the amount of conjugated afibrotic compound may be reported as equal to the value of total afibrotic compound. Otherwise, the concentration of conjugated afibrotic compound may be calculated by subtracting the amount of free afibrotic compound (e.g., calculated in Example 3) from the amount of total afibrotic compound (e.g., calculated in Example 2). This calculation can be represented by the formula: conjugated afibrotic compound (% w/w)=total afibrotic compound (% w/w)−free afibrotic compound (% w/w).

Converting amount of conjugated afibrotic compound in saline solution to the equivalent solid sample. The amount of conjugated afibrotic compound in a saline solution of modified polymer (e.g., afibrotic alginate) can be converted to the corresponding amount of conjugated afibrotic compound of its equivalent form as lyophilized solid, using a simple conversion. This conversion requires determining the concentration of the modified polymer (e.g., afibrotic alginate) in the saline solution, which can be obtained following the protocol outlined in Example 5. Then, simply dividing the amount of conjugated afibrotic compound obtained for the saline solution by the concentration of the modified polymer in the saline solution (multiplied by 100), one may derive the amount of conjugated afibrotic compound in the equivalent solid sample. This calculation is represented by the formula: conjugated afibrotic compound in solid sample (% w/w)=[conjugated afibrotic compound in saline (% w/w)]/([concentration of modified alginate in saline (% w/w)]×100).

For example, an afibrotic alginate in saline solution was calculated to have 1.97% w/w total afibrotic compound, and less than 0.01% w/w free afibrotic compound. As the amount of free afibrotic compound was less than 2%, the amount of conjugated afibrotic compound was determined to be 1.97% w/w (the same as total afibrotic compound). The concentration of the afibrotic alginate in the saline sample was determined to be 4.91% w/w (following the protocol in Example 5). The calculated amount of conjugated afibrotic compound in the corresponding solid sample was then calculated to be 40.12% w/w ([1.97% w/w]/[{4.91% w/w×100}]=40.12% w/w).

Example 5. Determining the Concentration of Modified Polymers in Solution Using Refractive Index Refractive index (RI) was used in order to determine the concentration of modified polymer (e.g., afibrotic alginates) in solution without removing the polymer modifications (e.g., afibrotic compounds) from the polymer (i.e., no acid hydrolysis was performed). In order to determine the concentration of the modified polymer in the saline solutions, a refractometer may be used. Here, the concentrations of afibrotic alginates were determined using a refractometer, following the protocol outlined below.

Standard Preparation. Approximately 1200 mg of the lyophilized solid form of a afibrotic alginate was weighed into a scintillation vial, and the actual weight (Ws) was recorded. A sterile saline solution was then added in an amount necessary to make a final concentration of 6.0%, and the actual final weight (Wt) was recorded. The mixture was then mixed gently with a tube rotator at 20 rpm for at least 2 hours, and then stored at 2-8° C. overnight to ensure sufficient dissolution. The next day, the sample was warmed to room temperature and gently mixed for at least 4 hours on a tube rotator at 20 rpm. The resulting 6.0% stock solution should be homogenous without any solid residue.

Dilutions. A series of dilutions carried out to prepare approximately 5 g solutions, at target concentrations of 5.5%, 5.0%, 4.5%, and 4.0%. For each concentration, the appropriate amount of the 6.0% stock solution prepared above was transferred to a vial, and the actual weight (Ws) was recorded. Then approximately 5000 mg of sterile saline solution was added, and the actual total weight (Wt) was recorded. Each vial was then gently mixed on a tube rotator at 20 rpm for at least an hour, and stored at 2-8° C. The actual weights, concentrations, and refractive index obtained for a triazole-modified alginate are provided in Table 2 below.

TABLE 2

Actual weights, concentrations, and refractive index (nD) of standard solutions.

| Nominal conc. (% w/w) | Actual Weight (Ws) (mg) | Actual Total Weight (Wt) (mg) | Actual conc. (% w/w) | Refractive Index (nD) |
|---|---|---|---|---|
| 6.0 | 1219.27 (solid) | 20237.83 | 6.024707194 | 1.3436 |
| 5.5 | 4575.38 (6%) | 5014.50 | 5.497123303 | 1.3428 |
| 5.0 | 4117.26 (6%) | 5001.45 | 4.959618899 | 1.3420 |
| 4.5 | 3751.35 (6%) | 5006.82 | 4.513999971 | 1.3413 |
| 4.0 | 3349.79 (6%) | 5008.61 | 4.029362221 | 1.3405 |

Refractometer measurement. At least 5 drops of the sample (at ambient temperature) were added to the clean and dry prism of a LAXCO RBD-5001 refractometer, such that the sample completely covers the prism bottom, and air bubbles on the prism were broken or removed. Measurements were obtained at a temperature of 20° C. Blank measurements were obtained by rinsing the prism twice with saline solution, and measuring the $2^{nd}$ saline rinse, which had an nD of 1.3343-1.3347. All measurements were obtained in triplicate.

Exemplary test sequence. The measurement of a series of samples was carried out with the following protocol. A saline solution was measured, followed by measuring the standard solution. Then, sample 1 was measured in triplicate, followed by each subsequent sample in triplicate. Finally, the standard was measured again, followed by saline. Between every measurement, the prism was rinsed.

Standard calibration curve. The refractive index (nD) measured for each of the standard solutions prepared above (the 6.0%, 5.5%, 5.0%, 4.5%, and 4.0% standard solutions) were plotted with against the calculated concentrations (shown in Table 2), and linear regression was performed to obtain the slope and Y-intercept.

Suitability criteria. The refractive index reading of 0.9% saline should be within 1.3343-1.3347; the calculated concentration should be within 90% to 110% of the theoretical concentration.

Standard curve extrapolation. Concentrations of samples were determined in one of two ways. In the first method, the concentration of each afibrotic alginate was determined by extrapolation from the standard curve. For example, concentrations of samples were calculated as follows: concentration=m×refractive index+b; where m is the slope of the linear fitted curve and b is the Y intercept. The coefficient of determination was no less than 0.95.

Determination of dn/dc: In a second method, concentrations of afibrotic alginates in solution were determined through comparison with a specific refractive index increment (i.e., dn/dc value). These values were calculated for both Compound 101 and a glucuronic acid moiety by first determining the actual concentration (μmol/g) or (% w/w) of each component (Compound 101 or glucuronic acid) using the actual Ws and Wt, then plotting against a corrected refractive index value. The dn/dc value is meant to be a constant for each component at a specific wavelength and temperature. For example, standard concentrations were quantified as follows;

Conc,stnd (mol/g)=Ws (mg)/MW (g/mol)/Wt (mg)*1,000,000; or

Conc,stnd (% w/w)=Ws (mg)/Wt (mg)*100

The corrected refractive index values were then calculated as follows:

RI, stnd—RI, saline=dn/dC*Conc, stnd, where, differential RI (dn/dC) is the slope of the linear fitted curve.

Exemplary dn/dc values are summarized in Table 3.

TABLE 3

Determination of dn/dc values

| Component | MW (g/mol) | dn/dc (g/mol) | Dn/dc (1/(% w/w)) |
|---|---|---|---|
| Glucuronic acid (GA) | 194.14 | 0.00002771 | 0.00142711 |
| Compound 101 | 587.60 | 0.00011501 | 0.00174782 |

Sample analysis: In order to calculate the total concentration of an afibrotic alginate in solution in this method, the refractive index value for a sample was measured (RI, sample) and used in the following equation to determine the afibrotic alginate concentration:

Concentration of unmodified alginate (% w/w or μmol/g)=[((RI, sample)−(RI, saline)−(dn/dc, Compound 101))×(concentration, Compound 101)]/(dn/dc, GA)

For example, concentration of an afibrotic alginate determined by RI is shown below:

TABLE 4

Exemplary calculation of afibrotic alginate concentration

| Description | Total (saline) | Residual free | Conj (saline) | Conc (Alginate) | % Conj (relative to modified alginate, weight ratio) | % Conj (relative to unmodified alginate, molar ratio) |
|---|---|---|---|---|---|---|
| Compound 101-alginate | 45.98 μmol/g | <0.01 w/w (LT 2% total) | 45.98 μmol/g (same as total) | 252.20 μmol/g | N/A | 45.98/252.20*100 = 18.23% |
| | 1.80% w/w | | 1.80% w/w (same as total) | 2.98% w/w | =1.80/(1.80 + 2.98)*100 = 37.68% | N/A |

Example 6: Preparation of Hydrogel Capsules

Capsules encapsulating RPE cells as single cells. Immediately before encapsulation, single ARPE-19 cells, engineered to express a therapeutic protein were centrifuged at 1,400 r.p.m. for 1 min and washed with calcium-free Krebs-Henseleit (KH) Buffer (4.7 mM KCl, 25 mM HEPES, 1.2 mM $KH_2PO_4$, 1.2 mM $MgSO_4 \times 7H_2O$, 135 mM NaCl, pH≈7.4, ≈290 mOsm). After washing, the cells were centrifuged again and all of the supernatant was aspirated. In some experiments, the cell pellet was then resuspended in the 70:30 CM-LMW-Alg:U-HMW-Alg solution (control capsules) or one of the modified alginate solutions described in Table 4 of Example 1 at the desired density of suspended single cells per ml alginate solution.

Prior to fabrication of one-compartment and two-compartment hydrogel capsules, buffers and alginate solutions were sterilized by filtration through a 0.2-μm filter using aseptic processes. For fabrication of one-compartment hydrogel capsules of about 1.5 mm diameter encapsulating cells, the desired number of cells were suspended in the desired alginate solution (e.g., the 70:30 CM-LMW-Alg:U-HMW-Alg solution used in Control capsules or one of the experimental alginate solutions described in Example 1) the resulting cell suspension was loaded into a syringe and capped with an 18-gauge blunt tipped needle (SAI Infusion Technologies). The syringe was placed onto a syringe pump oriented vertically above a dish containing a cross-linking solution. A high voltage power generator was connected to the needle and grounded to the biosafety cabinet. The syringe pump and power generator were turned on to extrude the alginate solution through the needle with a flow-rate of 0.16 mL/min or 10 mL/hr and adjusting the voltage in a range of 5-9 kV until there was a droplet rate of 12 droplets per 10 seconds.

To prepare devices configured as two-compartment hydrogel millicapsules of about 1.5 mm diameter, an electrostatic droplet generator was set up as follows: an ES series 0-100-kV, 20-watt high-voltage power generator (EQ series, Matsusada, NC, USA) was connected to the top and bottom of a coaxial needle (inner lumen of 22G, outer lumen of 18G, Ramé-Hart Instrument Co., Succasunna, NJ, USA). The inner lumen was attached to a first BD disposable 5-ml syringe with BD Luer-Lok™ tip (BD (Cat. No. 309646), Franklin Lakes, NJ, USA), which was connected to a syringe pump (Pump 11 Pico Plus, Harvard Apparatus, Holliston, MA, USA) that was oriented vertically. The outer lumen was connected via a luer coupling to a second 5-ml Luer-lock syringe which was connected to a second syringe pump (Pump 11 Pico Plus) that was oriented horizontally. To encapsulate cells only in the first (inner) compartment, a first alginate solution (70:30 CM-Alg-101:UM-Alg solution (as a control) or one of the experimental alginate solutions described in Example 1) comprising the cells (as single cell suspension) was placed in the first syringe and a second cell-free alginate solution comprising an afibrotic compound (e.g., a mixture of CM-LMW-Alg-101 and an U-HMW-Alg) was placed in the second syringe. For control 2-compartment hydrogel capsules in the Examples below, the second (outer) compartment was formed using the 70:30 CM-LMW-Alg-101:U-HMW-Alg solution. The two syringe pumps move the first and second alginate solutions from the syringes through both lumens of the coaxial needle and single droplets containing both alginate solutions are extruded from the needle into a glass dish containing a cross-linking solution. The settings of each Pico Plus syringe pump were 12.06 mm diameter and the flow rates of each pump were adjusted to achieve a flow rate ratio of 1:1 for the two alginate solutions. Thus, with the total flow rate set at 10 ml/h, the flow rate for each alginate solution was about 5 mL/h.

For fabrication of both the two-compartment and one-compartment millicapsules, after extrusion of the desired volumes of alginate solutions, the alginate droplets were crosslinked for five minutes in a cross-linking solution which contained 25 mM HEPES, 20 mM $BaCl_2$, 0.2M mannitol, and poloxamer 188. Capsules that had fallen to the bottom of the crosslinking vessel were collected by pipetting into a conical tube. After the capsules settled in the tube, the crosslinking buffer was removed, and capsules were washed. Capsules without cells were washed four times with HEPES buffer (NaCl 15.428 g, KCl 0.70 g, $MgCl_2 \cdot 6H_2O$ 0.488 g, 50 ml of HEPES (1 M) buffer solution (Gibco, Life Technologies, California, USA) in 2 liters of deionized water) and stored at 4° C. until use. Capsules encapsulating cells were washed four times in HEPES buffer, two times in 0.9% saline, and two times in culture media and stored in an incubator at 37° C.

EQUIVALENTS AND SCOPE

This application refers to various issued patents, published patent applications, journal articles, and other publications, all of which are incorporated herein by reference in their entirety. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present disclosure, as defined in the following claims.

The invention claimed is:

1. A method of evaluating a polymer composition, wherein the polymer composition comprises a polymer modified with:

(i) a compound of Formula (I-b):

(I-b)

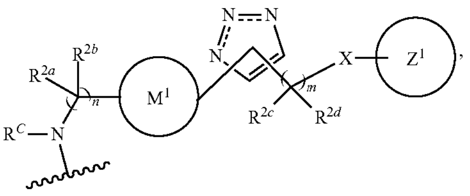, or a pharmaceutically acceptable salt thereof, wherein:

Ring $M^1$ is aryl or heteroaryl, wherein each aryl and heteroaryl is optionally substituted with one or more $R^3$;

Ring $Z^1$ is cycloalkyl, heterocyclyl, aryl, or heteroaryl, wherein each cycloalkyl, heterocyclyl, aryl, or heteroaryl is optionally substituted with 1-5 $R^5$;

each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group;

X is absent, O, or S;

each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with one or more halogen, oxo, cyano, cycloalkyl, or heterocyclyl; or two $R^5$ are taken together to form a 5-6 membered ring fused to Ring $Z^1$;

$R^C$ is hydrogen or alkyl;

each $R^{A1}$ and $R^{B1}$ is independently hydrogen, alkyl, or heteroalkyl;

m and n are each independently 1, 2, 3, 4, 5, or 6; and

“~” refers to a connection to the polymer; or (ii) a compound of Formula (III-a):

(III-a)

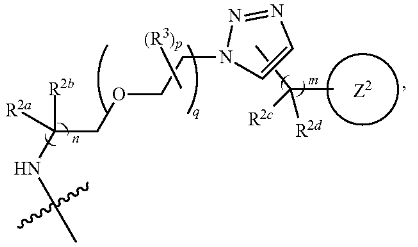

or a pharmaceutically acceptable salt thereof, wherein:

Ring $Z^2$ is cycloalkyl, heterocyclyl, aryl, or heteroaryl, each of which is optionally substituted with 1-5 $R^5$;

each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group;

each of $R^3$ and $R^5$ is independently alkyl, heteroalkyl, halogen, oxo, —$OR^{A1}$, —$C(O)OR^{A1}$, or —$C(O)R^{B1}$;

each $R^{A1}$ and $R^{B1}$ is independently hydrogen, alkyl, or heteroalkyl;

m and n are each independently 1, 2, 3, 4, 5, or 6;

and p are each independently 0, 1, 2, 3, 4, or 5;

q is an integer from 0 to 25; and

“~” refers to a connection to the polymer;

the method comprising:

(a) subjecting the polymer composition to reaction conditions that allow for release of the compound of Formula (I-b) or Formula (III-a) from the polymer; and (b) acquiring a value of concentration of the compound of Formula (I-b) or Formula (III-a) bound to the polymer, thereby evaluating the polymer composition.

2. The method of claim 1, wherein the polymer in the polymer composition is a polysaccharide.

3. The method of claim 2, wherein the polysaccharide is an alginate.

4. The method of claim 3, wherein the alginate:

(i) has an average molecular weight of 75 kD to 150 kD; or (ii) has a guluronate to mannuronate (G:M) ratio of greater than or equal to 1.5.

5. The method of claim 1, wherein the compound of Formula (I-b) or Formula (III-a) is covalently bound to the polymer in the modified polymer.

6. The method of claim 1, wherein the polymer composition comprises a single type of modified polymer.

7. The method of claim 1, wherein the compound of Formula (I-b) or Formula (III-a) is a compound selected from:

| Compound No. | Structure |
|---|---|
| 100 | 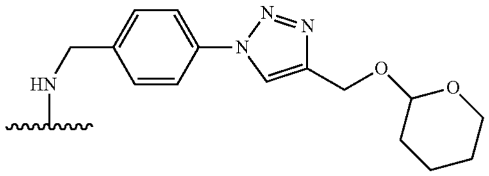 [SMILES: *NCc1ccc(-n2cc(COC3CCCCO3)nn2)cc1] |
| 101 | 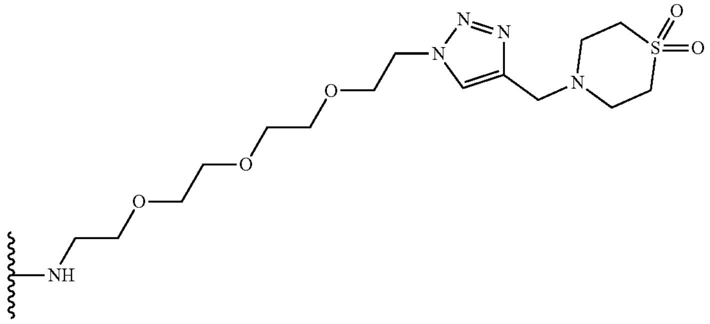 [SMILES: *NCCOCCOCCOCCn1cc(CN2CCS(=O)(=O)CC2)nn1] |

-continued
| Compound No. | Structure |
|---|---|
| 102 | 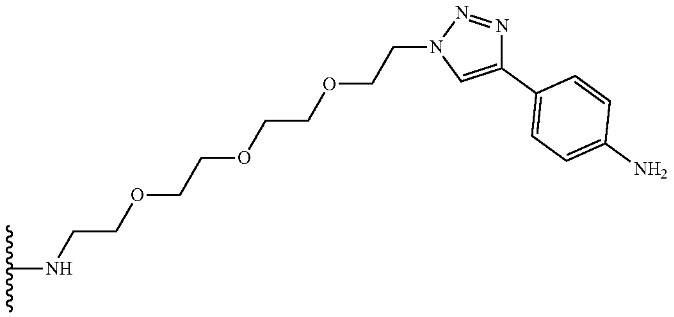 [SMILES: *NCCOCCOCCOCCn1cc(-c2ccc(N)cc2)nn1] |
| 103 | 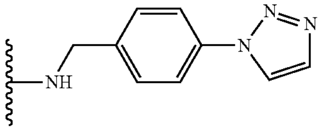 [SMILES: *NCc1ccc(-n2ccnn2)cc1] |
| 104 | 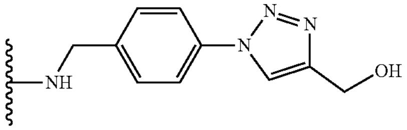 [SMILES: *NCc1ccc(-n2cc(CO)nn2)cc1] |
| 105 | 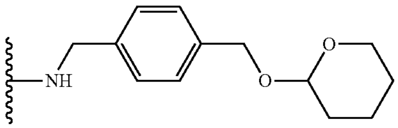 [SMILES: *NCc1ccc(COC2CCCCO2)cc1] |
| 106 | 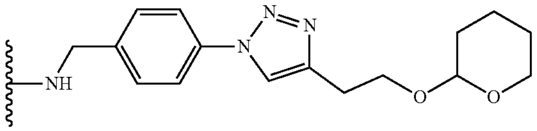 [SMILES: *NCc1ccc(-n2cc(CCOC3CCCCO3)nn2)cc1] |
| 107 | 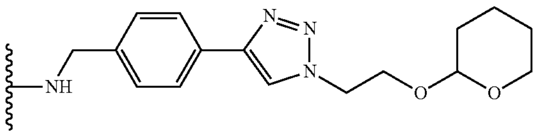 [SMILES: *NCc1ccc(-c2cn(CCOC3CCCCO3)nn2)cc1] |
| 108 | 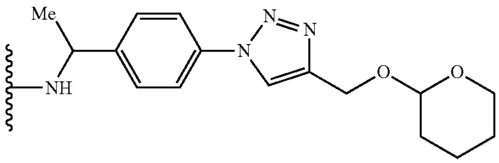 [SMILES: *NC(C)c1ccc(-n2cc(COC3CCCCO3)nn2)cc1] |
| 109 | 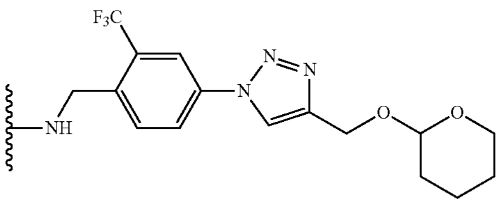 [SMILES: *NCc1ccc(-n2cc(COC3CCCCO3)nn2)cc1C(F)(F)F] |
| 110 | 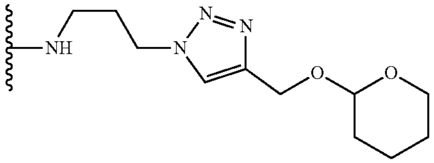 [SMILES: *NCCCn1cc(COC2CCCCO2)nn1] |

-continued
| Compound No. | Structure |
| --- | --- |
| 111 | 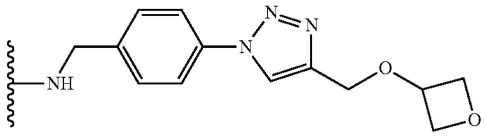 [SMILES: *NCc1ccc(-n2cc(COC3COC3)nn2)cc1] |
| 112 | 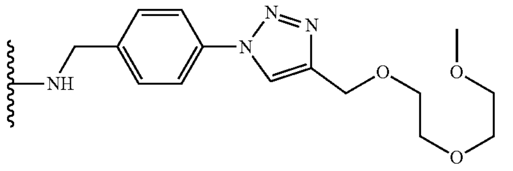 [SMILES: *NCc1ccc(-n2cc(COCCOCCOC)nn2)cc1] |
| 113 | 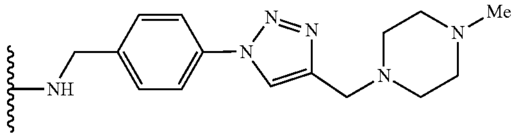 [SMILES: *NCc1ccc(-n2cc(CN3CCN(C)CC3)nn2)cc1] |
| 114 | 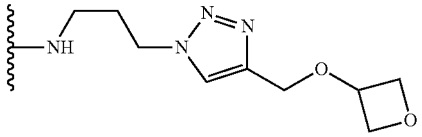 [SMILES: *NCCCn1cc(COC2COC2)nn1] |
| 115 | 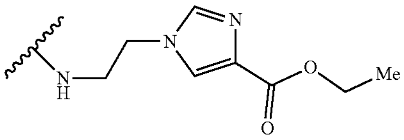 [SMILES: *NCCn1cnc(C(=O)OCC)c1] |
| 116 | 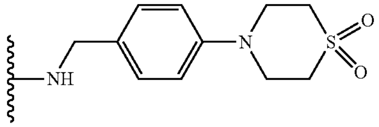 [SMILES: *NCc1ccc(N2CCS(=O)(=O)CC2)cc1] |
| 117 | 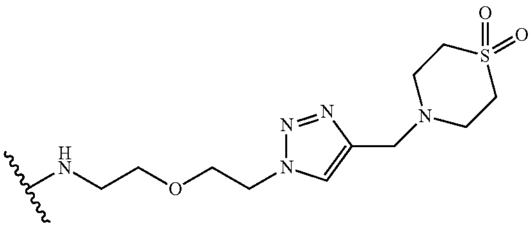 [SMILES: *NCCOCCn1cc(CN2CCS(=O)(=O)CC2)nn1] |
| 118 | 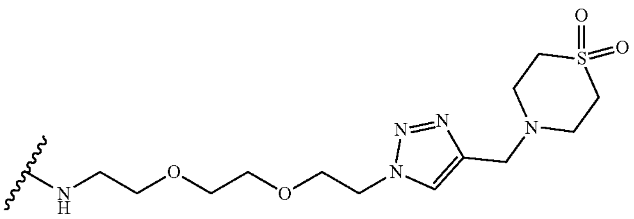 [SMILES: *NCCOCCOCCn1cc(CN2CCS(=O)(=O)CC2)nn1] |

-continued

| Compound No. | Structure |
| --- | --- |
| 119 | 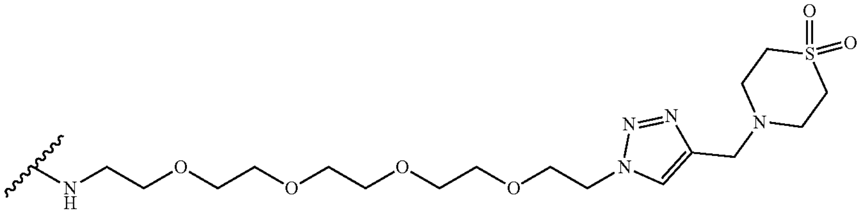 [SMILES: *NCCOCCOCCOCCOCCn1cc(CN2CCS(=O)(=O)CC2)nn1] |
| 120 | 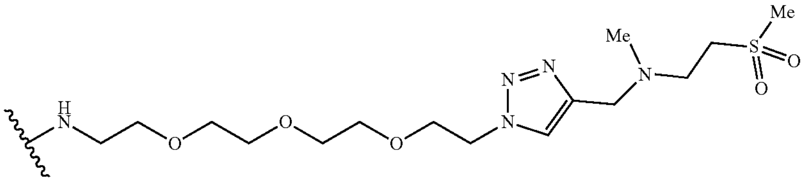 [SMILES: *NCCOCCOCCOCCn1cc(CN(C)CCS(C)(=O)=O)nn1] |
| 121 | 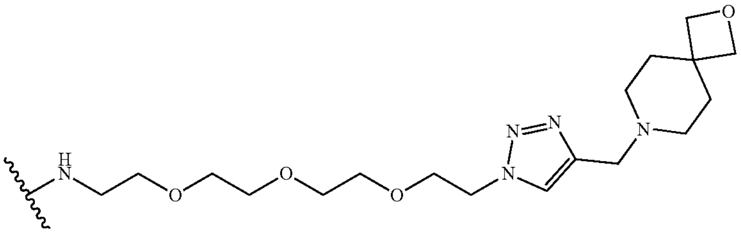 [SMILES: *NCCOCCOCCOCCn1cc(CN2CCC3(CC2)COC3)nn1] |

8. The method of claim 1, wherein the reaction conditions in step (a) comprise:

(i) contacting the polymer composition with an acidic solution; or (ii) heating the polymer composition; or (iii) exposing the polymer composition to microwave irradiation.

9. The method of claim 1, further comprising a separation step.

10. The method of claim 9, wherein the separation step occurs between step (a) and step (b).

11. The method of claim 9, wherein the separation step comprises chromatography.

12. The method of claim 1, wherein acquiring a value of concentration in step (b) comprises: (i) determining an area of a chromatogram peak for the compound of Formula (I-b) or Formula (III-a) and (ii) comparing an area of a chromatogram peak with a standard.

13. The method of claim 1, further comprising acquiring a value of concentration of an unconjugated compound of Formula (I-b) or an unconjugated compound of Formula (III-a) in the polymer composition.

14. The method of claim 13, wherein acquiring a value of concentration of the unconjugated compound of Formula (I-b) or the unconjugated compound of Formula (III-a) in the polymer composition comprises:

(a') separating the polymer composition into a polymer bound fraction and a non-polymer bound fraction;

(b') retaining the non-polymer bound fraction; and (c') acquiring a value of concentration of the unconjugated compound of Formula (I-b) or the unconjugated compound of Formula (III-a) in the non-polymer bound fraction.

15. The method of claim 14, wherein the separating of step (a') comprises filtration.

16. The method of claim 14, wherein step (c') comprises a separation step.

17. The method of claim 16, wherein the separation step comprises chromatography.

18. The method of claim 14, wherein acquiring a value of concentration in step (c') further comprises: (i) determining an area of a chromatogram peak of a sample of the unconjugated compound of Formula (I-b) or the unconjugated compound of Formula (III-a) in the non-polymer bound fraction and (ii) comparing an area of a chromatogram peak with a standard.

19. The method of claim 1, wherein evaluating a polymer composition comprises determining concentration of a compound of Formula (I-b) or Formula (III-a) bound to a modified polymer in the polymer composition.

20. The method of claim 19, wherein determining concentration of a compound of Formula (I-b) or Formula (III-a) bound to a modified polymer in the polymer composition comprises:

(a") acquiring a value for total concentration of the compound of Formula (I-b) or Formula (III-a) in the polymer composition;

(b") acquiring a value for concentration of an unconjugated compound of Formula (I-b) (or an unconjugated compound of Formula (III-a) in the polymer composition; and/or (c") subtracting the value of concentration of the unconjugated compound of Formula (I-b) or the unconjugated compound of Formula (III-a) from the value of total concentration of the compound of Formula (I-b) or Formula (III-a) in the polymer composition, thereby determining the concentration of the compound of Formula (I-b) or Formula (III-a) bound to a modified polymer in the polymer composition.

* * * * *